(12) United States Patent
Allinson et al.

(10) Patent No.: US 10,910,093 B2
(45) Date of Patent: *Feb. 2, 2021

(54) POST PROCEDURE CARE AND WELLNESS MANAGEMENT

(71) Applicant: Ceras Health, Inc., San Francisco, CA (US)

(72) Inventors: David Allinson, Danville, CA (US); Kathleen McCabe, Pleasanton, CA (US); Joel Garcia, San Francisco, CA (US); Kristina Redgrave, Burlingame, CA (US); Gurinder Virdi, Oakland, CA (US); Carlos Alvarez, Medellin, CO (US); Robert Dourandish, San Mateo, CA (US); Nikhil Mohan, San Francisco, CA (US); Imran Arshad, Lahore (PK); Kevin Murphy, Manhasset, NY (US); Reed Matheny, Berkeley, CA (US)

(73) Assignee: Ceras Health, Inc., San Francisco, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/298,744

(22) Filed: Mar. 11, 2019

(65) Prior Publication Data

US 2019/0206543 A1 Jul. 4, 2019

Related U.S. Application Data

(63) Continuation of application No. 14/542,345, filed on Nov. 14, 2014, now Pat. No. 10,232,201.

(Continued)

(51) Int. Cl.
*G16H 20/40* (2018.01)
*G06F 19/00* (2018.01)
*G16H 50/20* (2018.01)

(52) U.S. Cl.
CPC ......... *G16H 20/40* (2018.01); *G06F 19/3481* (2013.01); *G16H 50/20* (2018.01)

(58) Field of Classification Search
CPC ..... G16H 20/40; G16H 50/20; G06F 19/3481
See application file for complete search history.

(56) References Cited

U.S. PATENT DOCUMENTS

2001/0027472 A1  10/2001  Guan
2010/0286997 A1* 11/2010  Srinivasan ............. G06Q 50/22
                                                    705/2

(Continued)

*Primary Examiner* — Linh Giang Le
(74) *Attorney, Agent, or Firm* — Polsinelli

(57) ABSTRACT

Systems and methods for post procedure care and wellness management. A care network for a care recipient in providing post procedure care to the care recipient for a procedure performed on the care recipient is formed. A user specific care plan for the care recipient is generated, the user specific care plan including post procedure content and first post procedure care conditions associated with the post procedure content is generated for the care recipient. Whether the first post procedure care conditions are satisfied is determined. The post procedure content is sent to the care recipient through an internal communication channel. A first care data received notification comprising a generic notification lacking any personal health information of the care recipient is sent to the care recipient through an external communication channel. The care recipient is logged in to view the post procedure content through the internal communication channel.

20 Claims, 14 Drawing Sheets

Related U.S. Application Data

(60) Provisional application No. 61/962,718, filed on Nov. 14, 2013.

(56) References Cited

U.S. PATENT DOCUMENTS

| 2011/0246219 A1* | 10/2011 | Smith | G06Q 10/087 |
| | | | 705/2 |
| 2012/0101847 A1* | 4/2012 | Johnson | G06Q 10/00 |
| | | | 705/3 |

* cited by examiner

POST PROCEDURE CARE AND WELLNESS MANAGEMENT

CROSS-REFERENCE TO RELATED APPLICATIONS

The present application is a continuation of U.S. Non-Provisional patent application Ser. No. 14/542,345, filed Nov. 14, 2014, and entitled "POST PROCEDURE CARE AND WELLNESS MANAGEMENT," which claims the benefit of U.S. Provisional Patent Application Ser. No. 61/962,718, filed Nov. 14, 2013, and entitled "METHOD FOR COLLECTING PROPRIETARY POPULATION HEALTH DATA THROUGH UTILIZATION OF A CLOUD-BASED AND MOBILE SERVICE BY USERS OF DIFFERING ROLLS," which is incorporated by reference herein.

BACKGROUND

An area of ongoing research and development is post procedure care management and wellness management. In particular there are problems that exist with implementing systems and methods that are compliant with the health insurance portability and compliance act (hereinafter referred to as "HIPAA").

Other limitations of the relevant art will become apparent to those of skill in the art upon a reading of the specification and a study of the drawings.

SUMMARY

The following implementations and aspects thereof are described and illustrated in conjunction with systems, tools, and methods that are meant to be exemplary and illustrative, not necessarily limiting in scope. In various implementations one or more of the above-described problems have been addressed, while other implementations are directed to other improvements.

Various implementations include systems and methods for post procedure care and wellness management. In various implementations, a care network for a care recipient in providing post procedure care to the care recipient for a procedure performed on the care recipient is formed. Further, in various implementations, a user specific care plan for the care recipient, the user specific care plan including post procedure content and first post procedure care conditions associated with the post procedure content is generated for the care recipient. In various implementations, whether the first post procedure care conditions are satisfied is determined. In various implementations, the post procedure content is sent to the care recipient through an internal communication channel if it is determined that the first post procedure care conditions are met. Additionally, in various implementations, a first care data received notification is sent to the care recipient through an external communication channel, the first care data received notification being a generic notification lacking any personal health information of the care recipient. In various implementations, the care recipient is logged in to view the post procedure content through the internal communication channel.

These and other advantages will become apparent to those skilled in the relevant art upon a reading of the following descriptions and a study of the several examples of the drawings.

DETAILED DESCRIPTION

Figure 1:
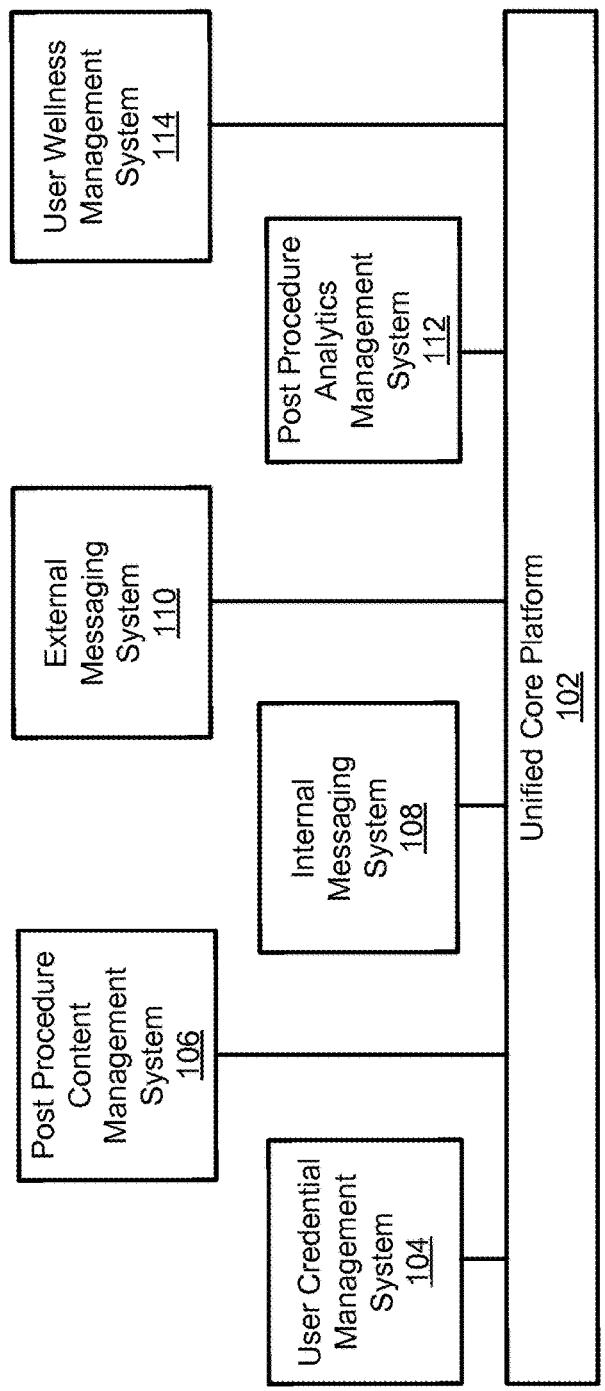
FIG. 1 depicts a diagram of an example of a system for maintaining communication of content used in providing either or both post procedure care and user wellness.

FIG. 1 depicts a diagram 100 of an example of a system for maintaining communication of content used in providing either or both post procedure care and user wellness. The system of the example of FIG. 1 includes a unified core platform 102, a user credential management system 104, a post procedure content management system 106, an internal messaging system 108, an external messaging system 110, a post procedure analytics management system 112, and a user wellness management system 114. Depending upon implementation-specific or other considerations, one or a combination of the unified core platform 102, the user credential management system 104, the post procedure content management system 106, the internal messaging system 108, the external messaging system 110, the post procedure analytics management system 112, and the user wellness management system 114 can be integrated or implement procedures in compliance with HIPAA standards.

The unified core platform functions to couple the user credential management system 104, the post procedure content management system 106, the internal messaging system 108, the external messaging system 110, the post procedure analytics management system 112, and the user wellness management system 114. In coupling the user credential management system 104, the post procedure content management system 106, the internal messaging system 108, the external messaging system 110, the post procedure analytics management system 112, the wellness management system 114 to each other, the unified core platform can exchange data and/or distribute functions used in maintaining communication of content used in providing either or both post procedure care and user wellness. The unified core platform 102 can be implemented as a computer-readable medium or part of a computer-readable medium. As used in this paper, a "computer-readable medium" is intended to include all mediums that are statutory (e.g., in the United States, under 35 U.S.C. 101), and to specifically exclude all mediums that are non-statutory in nature to the extent that the exclusion is necessary for a claim that includes the computer-readable medium to be valid. Known statutory computer-readable mediums include hardware (e.g., registers, random access memory (RAM), non-volatile (NV) storage, to name a few), but may or may not be limited to hardware.

A computer-readable medium, as is used in this paper, is intended to represent a variety of potentially applicable technologies. For example, a computer-readable medium can be used to form a network or part of a network. Where two components are co-located on a device, the computer-readable medium 102 can include a bus or other data conduit or plane. Where a first component is co-located on one device and a second component is located on a different device, a computer-readable medium can include a wireless or wired back-end network or LAN. A computer-readable medium can also encompass a relevant portion of a WAN or other network, if applicable.

The unified core platform 102, the user credential management system 104, the post procedure content management system 106, the internal messaging system 108, the external messaging system 110, the post procedures analytics management system 112, the user wellness management system 114, and other applicable systems, or devices described in this paper can be implemented as a computer system, a plurality of computer systems, or parts of a computer system or a plurality of computer systems. A computer system, as used in this paper, is intended to be construed broadly. In general, a computer system will include a processor, memory, non-volatile storage, and an interface. A typical computer system will usually include at least a processor, memory, and a device (e.g., a bus) coupling the memory to the processor. The processor can be, for example, a specific-purpose central processing unit (CPU), such as a microprocessor, or a special-purpose processor, such as a microcontroller.

The memory can include, by way of example but not limitation, random access memory (RAM), such as dynamic RAM (DRAM) and static RAM (SRAM). The memory can be local, remote, or distributed. The bus can also couple the processor to non-volatile storage. The non-volatile storage is often a magnetic floppy or hard disk, a magnetic-optical disk, an optical disk, a read-only memory (ROM), such as a CD-ROM, EPROM, or EEPROM, a magnetic or optical card, or another form of storage for large amounts of data. Some of this data is often written, by a direct memory access process, into memory during execution of software on the computer system. The non-volatile storage can be local, remote, or distributed. The non-volatile storage is optional because systems can be created with all applicable data available in memory.

Software is typically stored in the non-volatile storage. Indeed, for large programs, it may not even be possible to store the entire program in the memory. Nevertheless, it should be understood that for software to run, if necessary, it is moved to a computer-readable location appropriate for processing, and for illustrative purposes, that location is referred to as the memory in this paper. Even when software is moved to the memory for execution, the processor will typically make use of hardware registers to store values associated with the software, and local cache that, ideally, serves to speed up execution. As used herein, a software program is assumed to be stored at an applicable known or convenient location (from non-volatile storage to hardware registers) when the software program is referred to as "implemented in a computer-readable storage medium." A processor is considered to be "configured to execute a program" when at least one value associated with the program is stored in a register readable by the processor.

In one example of operation, a computer system can be controlled by operating system software, which is a software program that includes a file management system, such as a disk operating system. One example of operating system software with associated file management system software is the family of operating systems known as Windows® from Microsoft Corporation of Redmond, Wash., and their associated file management systems. Another example of operating system software with its associated file management system software is the Linux operating system and its associated file management system. The file management system is typically stored in the non-volatile storage and causes the processor to execute the various acts required by the operating system to input and output data and to store data in the memory, including storing files on the non-volatile storage.

The bus can also couple the processor to the interface. The interface can include one or more input and/or output (I/O) devices. The I/O devices can include, by way of example but not limitation, a keyboard, a mouse or other pointing device, disk drives, printers, a scanner, and other I/O devices, including a display device. The display device can include, by way of example but not limitation, a cathode ray tube (CRT), liquid crystal display (LCD), or some other applicable known or convenient display device. The interface can include one or more of a modem or network interface. It will be appreciated that a modem or network interface can be considered to be part of the computer system. The interface can include an analog modem, isdn modem, cable modem, token ring interface, satellite transmission interface (e.g. "direct PC"), or other interfaces for coupling a computer system to other computer systems. Interfaces enable computer systems and other devices to be coupled together in a network.

The computer systems can be compatible with or implemented as part of or through a cloud-based computing system. As used in this paper, a cloud-based computing system is a system that provides virtualized computing resources, software and/or information to client devices. The computing resources, software and/or information can be virtualized by maintaining centralized services and resources that the edge devices can access over a communication interface, such as a network. "Cloud" may be a marketing term and for the purposes of this paper can include any of the networks described herein. The cloud-based computing system can involve a subscription for services or use a utility pricing model. Users can access the protocols of the cloud-based computing system through a web browser or other container application located on their client device.

A computer system can be implemented as an engine, as part of an engine, or through multiple engines. As used in this paper, an engine includes at least two components: 1) a dedicated or shared processor and 2) hardware, firmware, and/or software modules that are executed by the processor. Depending upon implementation-specific or other considerations, an engine can be centralized or its functionality distributed. An engine can include special purpose hardware, firmware, or software embodied in a computer-readable medium for execution by the processor. The processor transforms data into new data using implemented data structures and methods, such as is described with reference to the FIGs. in this paper.

The engines described in this paper, or the engines through which the systems and devices described in this paper can be implemented, can be cloud-based engines. As used in this paper, a cloud-based engine is an engine that can run applications and/or functionalities using a cloud-based computing system. All or portions of the applications and/or functionalities can be distributed across multiple computing devices, and need not be restricted to only one computing device. In some embodiments, the cloud-based engines can execute functionalities and/or modules that end users access through a web browser or container application without having the functionalities and/or modules installed locally on the end-users' computing devices.

As used in this paper, datastores are intended to include repositories having any applicable organization of data, including tables, comma-separated values (CSV) files, traditional databases (e.g., SQL), or other applicable known or convenient organizational formats. Datastores can be implemented, for example, as software embodied in a physical computer-readable medium on a general- or specific-purpose machine, in firmware, in hardware, in a combination thereof, or in an applicable known or convenient device or system. Datastore-associated components, such as database interfaces, can be considered "part of" a datastore, part of some other system component, or a combination thereof, though the physical location and other characteristics of datastore-associated components is not critical for an understanding of the techniques described in this paper.

Datastores can include data structures. As used in this paper, a data structure is associated with a particular way of storing and organizing data in a computer so that it can be used efficiently within a given context. Data structures are generally based on the ability of a computer to fetch and store data at any place in its memory, specified by an address, a bit string that can be itself stored in memory and manipulated by the program. Thus, some data structures are based on computing the addresses of data items with arithmetic operations; while other data structures are based on storing addresses of data items within the structure itself. Many data structures use both principles, sometimes combined in non-trivial ways. The implementation of a data structure usually entails writing a set of procedures that create and manipulate instances of that structure. The datastores, described in this paper, can be cloud-based datastores. A cloud-based datastore is a datastore that is compatible with cloud-based computing systems and engines.

In a specific implementation, the user credential management system 104 functions to manage user credentials for authenticating users in accessing one or a combination of the systems and or engines described in this paper. Depending upon implementation-specific or other considerations, user credentials can include a user identification, a user name, a user password, and/or a user token. In managing user credentials, the user credential management system 104 can receive and/or identify user credentials used for providing a user access. Further, in managing user credentials, the user credential management system 104 can verify whether provided user credentials match user credentials for providing a user access.

In a specific implementation, the user credential management system 104 functions to manage a care network for an individual. A care network, as used in this paper, includes a network of care providers or users that are selected by a user for providing and/or maintaining either or both post procedure care to a user or wellness for a user, who is a care recipient. Depending upon implementation-specific or other considerations, a care network can be a private network of users who can communicate with each other or select users who are within the care network. For example, a care network can include a doctor who performs a procedure on a patient and family members of the patient who provide care to the patient after the procedure is performed. Further depending upon implementation-specific or other considerations, users and/or care providers within a care network can communicate, or otherwise send and/or receive data privately through an applicable system for transmitting data between individuals within the care network, such as the internal messaging systems described in this paper. In communicating privately, only specific people can send and receive data between each other, for example only individuals within a care network and/or specific individuals within a care network can send and receive care data between each other for a given instance of the care network.

In a specific implementation, a procedure, for which post procedure care is provided and/or maintained includes a medical procedure provided to a user. For example, a procedure can include a surgery performed on a user. In another example, a procedure can include a long-term care procedure performed on a user, such as monitoring the user's cholesterol levels. Depending upon implementation-specific or other considerations, a time during which post procedure care is provided can include the time immediately following a performance of a procedure on a user, the time after a user is discharged from a hospital or an appropriate medical care technician after performance of a procedure on the user, and/or the time during which one or a plurality of procedures are performed on a user.

In a specific implementation, the post procedure content management system 106 functions to manage post procedure content used in providing and maintaining post procedure care to a user. As used in this paper, post procedure content includes data that is sent to at least one user in a care network in providing and/or maintaining post procedure care to a user. Depending upon implementation-specific or other considerations, post procedure content can include care alerts. Care alerts can include reminders of tasks a user needs to perform in providing and maintaining post procedure care. For example, a care alert can be a reminder that a user needs to take a measurement of their blood pressure. In another example, a care alert can be a reminder that a care provider needs to administer medication to a patient. Further depending upon implementation-specific or other considerations, post procedure content can include suggested media used to aid a user in recovering from a procedure. For example, if a user has a procedure performed on them for fixing a broken leg, then post procedure content can include images and/or videos of rehabilitation exercises for the broken leg. Depending upon implementation-specific or other considerations, post procedure content can include content used to engage and/or gauge the progress of a user in post procedure care. For example, if a procedure is performed on a user for fixing a broken leg, then post procedure content can include questions assessing a degree to which the user has healed after the procedure. Further depending upon implementation-specific or other considerations, post procedure content can include requests for data from a user in managing post procedure care. For example, post procedure content can include a request for a blood pressure reading of a user. The post procedure content management system 106 can collect post procedure content from users within a care network, e.g. a doctor who performed a procedure, templates of standard post procedure content presented to users who undergo a specific procedure, and/or third party sources who provide post procedure content.

In a specific implementation, the post procedure content management system 106 functions to determine post procedure care conditions used in providing and/or maintaining post procedure care to a user. A post procedure care condition, as is used in this paper, includes a condition for sending post procedure content to a user and which users to send port procedure content within a care network in providing and/or maintaining post procedure care. Depending upon implementation-specific or other considerations, a post procedure care condition can specify to send post procedure content to a user after a specific amount of time. For example, a post procedure care condition can specify to send post procedure content after two weeks have passed since the procedure was performed on a user. Further depending upon implementation-specific or other considerations, a post procedure care condition can specify to send post procedure content if a certain occurrence is not met. For example, a post procedure care condition can specify to send a reminder for a blood pressure reading if a blood pressure reading is not received within a certain amount of time. Depending upon implementation-specific or other considerations, a post procedure care condition can specify to send post procedure content if a certain event occurs. For example, a post procedure care condition can specify to send a notice to a care giver if a user's weight is above a predetermined amount.

In a specific implementation, in managing post procedure content, the post procedure content management system 106 can manage a care plan for a user. A care plan for a user can include post procedure content that can be sent to a user and post procedure care conditions that identify whether the post procedure content should be sent to the user. Depending upon implementation-specific or other considerations, in managing a care plan for a user, the post procedure content management system 106 can either or both generate and update the care plan for the user.

In a specific implementation, the internal messaging system 108 functions to transmit data through internal communication channels to users within a care network for either or both providing post procedure care to a user and wellness to the user. Internal communication channels include communication channels in which a user must login to view data sent through the internal communication channels and send data through the internal communication channels. In transmitting data to users within a care network, the internal messaging system 108 can transmit post procedure content to the users within the care network. Further, in transmitting data to users within a care network, the internal messaging system 108 can determine whether post procedure care conditions are met and subsequently transmit post procedure content according to the post procedure care conditions. Depending upon implementation-specific or other considerations, the internal messaging system 108 can directly transmit post procedure content to an account associated with a user and/or publish post procedure content on a feed through which one or a plurality of users within a care network can view the published post procedure content. In directly transmitting post procedure content to an account associated with a user, the internal messaging system 108 can provide peer-to-peer chat or group chat functioning. Further depending upon implementation-specific or other considerations, a user has to login using their credentials through the user credential management system 104 in order to view post procedure content transmitted to either them or published on a feed. As a result of requiring a user to login to their account to view transmitted post procedure content, the internal messaging system 108 is compliant with HIPAA standards.

In a specific implementation, the internal messaging system 108 functions to receive care data from users within a care network and transmit received care data to users within the care network. Care data can include post procedure content, data related to care of a patient, and or data generated in response to post procedure content. For example, care data can include a video that a doctor wants their patient to view. In another example, care data can include measured vital statistics of a patient, as taken by a care giver for the patient in response to a care alert requesting that the vital statistics of the patient be taken. Care data can have associated post procedure care conditions that dictate whether the care data can be transmitted and/or published, and which users to send the care data to or are allowed to access the care data. Depending upon implementation-specific or other considerations, the internal messaging system 108 can directly transmit care data to an account associated with a user and/or publish care data on a feed through which one or a plurality of users within a care network can view the care content.

In a specific implementation, the internal messaging system 108 can receive care data from a device of a user, an application, and/or a service. Depending upon implementation-specific or other considerations, the internal messaging system 108 can receive care data from a wearable device of a user. Examples of wearable devices include Basis Band®, Body Media Cora®, Body Media Link®, Fitbit Flex®, Fitbit Force®, Fitbit One®, Jawbone UP®, Jawbone UP24®, Nike Fuel Band®, Fitbug Orb®, Fitbug Air®, Fitbug Go®, Withings Pulse®, Pebble Original®, Pebble Steel®, iHealth Activity Tracker®, Lumoback®, Omron®, and iHeart Omron®. Example of devices of a user include computers, smart phones, laptops, Fitbit Aria Scale®, Fitbug WoW Scale®, Withings Scale®, Glooko®, iHealth Blood Glucose Monitor®, iHealth BP Monitor®, Withings BP Monitor®, iHealth Pulse Oximeter®, and Vitadock®. Example of application from which the internal messaging system 108 can receive care data from include Dailymile®, Mapmyfitness®, Moves App®, RunKeeper®, Strava®, ManageBGL®, Fatsecret®, and Fleetly®.

In a specific implementation, the external messaging system 110 functions to send care data received notifications to users within a care network through communication channels external from internal communication channels used by the internal message system 108. Communication channels external from the internal message system 108 can include an applicable communication channel separate from an internal communication channel used by the internal messaging system 108. Examples of communication channels external from the internal message system include email supported by third parties and short message service (hereinafter referred to as "SMS"). The external messaging system 110 can send a notification, e.g. a push notification, to a user within a care network over a communication channel external from the internal messaging system 108 when a user receives either or both post procedure content and care data through the internal messaging system 108. For example, if a doctor receives care data including vital statistics of a patient through the internal messaging system 108, then the external messaging system 110 can send a notification to the doctor indicating that the doctor has received care data. Care data received notification sent by the external messaging system 110 can be generic in that they do not contain any protected health information of users within a care network and only notify a user that they have received care data through the internal messaging system 108. For example, a care data received notification sent to a user by the external messaging system can indicate only that care data and/or post procedure content has been received by an account of the user, and not include anything included in the received care and/or post procedure content. As a result, in sending care data received notifications that are generic, the external messaging system 110 can be compliant with HIPAA standards.

In a specific implementation, the post procedure analytics management system 112 functions to generate analytics reports for data sent within a care network for providing and/or maintaining post procedure care. Depending upon implementation-specific or other considerations, the post procedure analytics management system 112 can generate analytics reports for post procedure care based on either or both post procedure content and care data sent within a care network.

In a specific implementation, the user wellness management system 114 functions to provide and/or maintain wellness for a user. In providing and/or maintaining wellness for a user the user wellness management system 114 can manage a wellness network of a user. Users within a wellness network of a user can communicate using the internal messaging system 108. Further, in providing and/or maintaining wellness for a user, the user wellness management system 114 can perform a health risk assessment and log activities of a user for maintaining or increasing wellness of the user. Additionally, the user wellness management system 114 can present challenge to a user that if performed, improve the wellness of the user.

Figure 2:
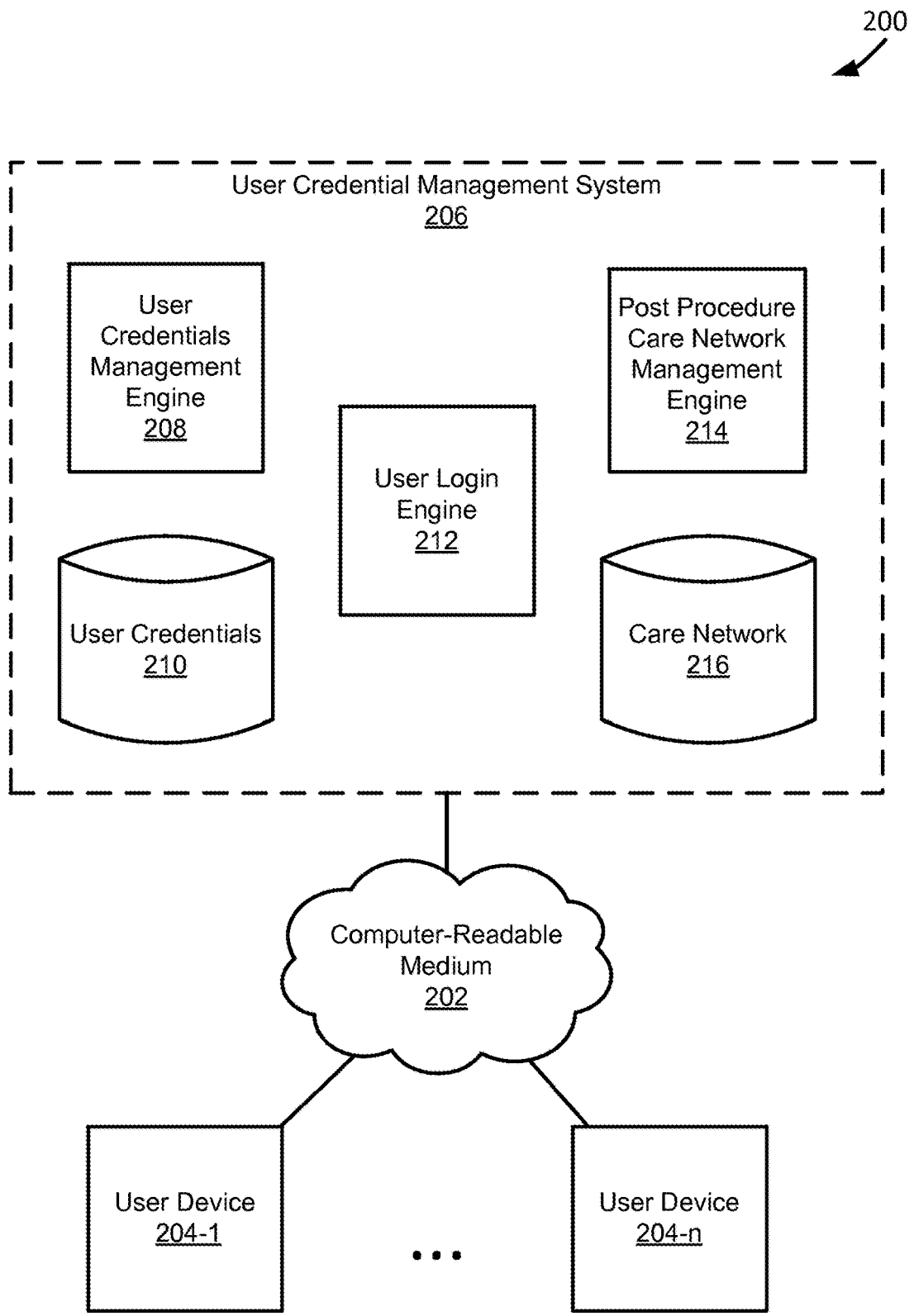
FIG. 2 depicts a diagram of an example of a system for managing user credentials in providing and/or maintaining post procedure care for a user through a care network of the user.

FIG. 2 depicts a diagram 200 of an example of a system for managing user credentials in providing and/or maintaining post procedure care for a user through a care network of the user. The example system shown in FIG. 2, includes a computer-readable medium 202, user devices 204-1 . . . 204-n (hereinafter referred to as "user devices 204"), and a user credential management system 206. In the example system shown in FIG. 2, the user devices 204 and the user credential management system 206 are coupled to each other through the computer-readable medium 202.

In a specific implementation, the user devices 204 functions according to applicable devices of a user for sending and receiving data used in providing and/or maintaining post procedure care for a user through a care network of the user. The user devices 204 can be associated with a user who is the subject of a care network, and/or users within the care network of the user. The user devices 204 can be used to send user credentials and/or receive care network enrollment requests by a user. Care network enrollment requests include requests for a user to accept a request to join a care network and/or provide credentials for enrolling to join a care network. For example, if a patient wishes to add family members to a care network, then user devices 204 of the family members can be used to receive care network enrollment requests by the family members. Depending upon implementation-specific or other considerations, the user devices 204 can be thin client devices or ultra-thin client devices. Further depending upon implementation-specific or other considerations, the user devices 204 can include wireless or cellular network interfaces through which the user devices 204 can be wirelessly connected to the computer-readable medium 202.

In a specific implementation, the user credential management system 206 functions according to an applicable system for managing user credentials in providing and/or maintaining post procedure care to a user through a care network of the user, such as the user credential management systems described in this paper. In managing user credentials, the user credential management system can receive and/or assign user credentials for logging a user in to view and or transmit data through an applicable system for internally transmitting data used in providing and/or maintain post procedure care of a user through a care network of the user, such as the internal messaging systems described in this paper. Further, in managing user credentials, the user credential management system 206 can send enrollment requests to users for enrolling and/or joining a care network. In managing user credentials, the user credential management system 206 can log in a user for viewing and or transmitting data used in providing and/or maintaining post procedure care by receiving user credentials from a user and authenticating the user credentials.

In a specific implementation, the user credential management system 206 functions to manage a care network of a user. In managing a care network of a user, the user credential management system 206 can add, update, and/or remove users from the care network of the user. Depending upon implementation-specific or other considerations, the user credential management system 206 can add, update, and/or remove users from the care network of a user based on instructions received from the user. For example, a user can send instructions specifying to add a family member to a care network, and the user credential management system 206 can add the family member to the care network. In managing a care network based on instructions from a user that the care network is created for, the user credential management system 206 functions in compliance with HIPAA standards. Further depending upon implementation-specific or other considerations, the user credential management system 206 can suggest users to add to a care network. For example, if a doctor performed a procedure patient, then the user credential management system 206 can suggest to the user that the doctor be included in the care network of the patient. In managing a care network of a user, the user credential management system 206 can require that the user login using their credentials in providing security and compliance with HIPAA standards. Further in managing a care network of a user, the user credential management system 206 can send enrollment requests to users added to a care network.

In the example system shown in FIG. 2, the user credential management system 206 includes a user credentials management engine 208, a user credentials datastore 210, a user login engine 212, a post procedure care network management engine 214, and a care network datastore 216. In a specific implementation, the user credentials management engine functions to manage user credentials for logging a user in to view and or transmit data through an applicable system for internally transmitting data used in providing and/or maintain post procedure care of a user through a care network of the user, such as the internal messaging systems described in this paper. In managing user credentials, the user credential management engine 208 can assign user credentials to a user for registering a user. For example, if a patient is using the system for the first time to set up a care network for providing and maintaining post procedure care, then the user credentials management engine 208 can assign user credentials to the user. Depending upon implementation-specific or other considerations, in assigning user credentials to a user, the user credentials management engine 208 can provide an access token and or certificates to user devices 204 of the user for logging in the user.

In a specific implementation, the user credential datastore 210 functions to store user credentials assigned to a user by the user credentials management engine 208. User credentials stored in the user credentials datastore 210 can be used to authenticate a user in accessing an internal messaging system for viewing and/or sending care data used in providing and/or maintaining post procedure care for a user through a care network of the user. User credentials stored in the user credentials datastore 210 can be stored as encrypted data at the file level, as in compliance with HIPAA standards. Further in compliance with HIPAA standards, the user credential datastore 210 can be accessible through at least two factor authentication. For example, the user credential datastore 210 can be accessed through a secure socket layer virtual private network (hereinafter referred to as "SSL VPN") implementing at least two factor authentication.

In a specific implementation, the user login engine 212 functions to log in a user for access to an internal messaging system for viewing and/or sending care data in providing post procedure care to a user through a care network of the user. In logging in a user for access to an internal messaging system, the user login engine 212 can receive user credentials of a user from the user devices 204 of the user when the user attempts to log in for accessing the internal messaging system. Further, in logging in a user for access to an internal messaging system, the user login engine 212 can compare received user credentials of a user with user credentials of the user stored in the user credentials datastore 210 in order to authenticate the user. If the user is authenticated, the user login engine 212 can provide the user with access to an internal messaging system for viewing and/or sending care data in providing post procedure care to a user through a care network of the user.

In a specific implementation, the user login engine 212 functions to logout a user from access to an internal messaging system for viewing and/or sending care data in providing post procedure care to a user through a care network of the user. In logging out a user from access to an internal messaging system, the user login engine 212 can determine whether a user is inactive in interacting with internal messaging system and determining an amount of time that the user has remain inactive. The user login engine 212 can determine to logout a user from accessing an internal messaging system if the user has remained inactive with the internal messaging system for a specific amount of time. For example, the user login engine 212 can logout a user from accessing an internal messaging system if the user has remained inactive with the internal messaging system for 5 or more minutes. In logging out a user from accessing an internal messaging system for viewing and/or sending care data in providing post procedure care to a user through a care network of the user, the user login engine 212 is in compliance with HIPAA standards.

In a specific implementation, the post procedure care network management engine 214 functions to manage a care network of a user. In managing a care network of a user, the post procedure care network management engine 214 can add, update, and/or delete users from a care network of a user. The post procedure care network management engine 214 can manage a care network of a user based on instructions received from the user. Instructions received from a user can include whether to add or delete a user from a care network, and/or what care data the user in the care network can view and/or transmit. For example, if the user sends instructions to add a family member to their care network, then the post procedure care network management engine 214 can add the family member to the care network. In another example, if the user sends instructions to remove a family member from their care network, then the post procedure care network management engine 214 can remove the family member from the care network.

Depending upon implementation-specific or other considerations, the post procedure care network management engine 214 can suggest users to add to a care network. For example if a doctor performed a procedure on a patient, then the post procedure care network management engine 214 can suggest a user to add to a care network. Data used in managing a care network, including either or both instructions used in managing a care network of a user, and suggested users for the care network, can be sent between the post procedure care network management engine 214 and user devices 204 of a user through either or both applicable internal messaging systems and external messaging systems, such as the internal and external messaging systems described in this paper.

In a specific implementation, the care network datastore 216 functions to store care network data describing a care network of a user as managed by the post procedure care network management engine 214. Care network data can include an identification of users within a care network, what care data can be sent to which users within the care network in accordance with satisfaction of post procedure care conditions for the care data, and/or external communication channels through which users can receive data outside of an internal messaging system. Care network data stored in the care network datastore 216 can be generated by the post procedure care network management engine 214 in conjunction with the management of a care network. For example if a user is added to a care network, then the post procedure care network management engine 214 can modify care network data stored in the care network datastore 216 to identify the user added to the care network and/or what care data can be sent to the user in accordance with satisfaction of post procedure care conditions for the care data. Care network data stored in the care network datastore 216 can be stored as encrypted data at the file level, as in compliance with HIPAA standards. Further in compliance with HIPAA standards, the care network datastore 216 can be accessible through at least two factor authentication. For example, the care network datastore 216 can be accessed through an SSL VPN implementing at least two factor authentication.

In a specific implementation, the user credentials management engine 208 can manage user credentials based on managing of a care network by the post procedure care network management engine 214. In managing user credentials based on managing of a care network by the post procedure care network management engine 214, the user credentials management engine can send enrollment requests to users who are added to a care network by the post procedure care network management engine 214. For example, if a patient adds a family member to a care network, then the user credentials management engine 208 can send an enrollment request to the family member. Depending upon implementation-specific or other considerations, the user credential management engine 208 can assign user credentials to a user that the user can utilize in accessing an internal messaging system for viewing and/or sending care data for providing post procedure care to the user through a care network of the user. In managing user credentials based on managing of a care network by the post procedure care network management engine 214, the user credentials management engine 208 can update user credentials in the user credentials datastore 210. For example, if a user is added to a care network and the user credentials management engine 208 assigns user credentials to the user, then the user credentials management engine 208 can update the user credentials in the user credentials datastore 210 to include the assigned credentials. In another example, if a user is removed from a care network, then the user credentials management engine 208 can update the user credentials in the user credentials datastore 210 to delete the user credentials of the removed user.

In an example of operation of the example system shown in FIG. 2, the user credentials management engine 208 assigns user credentials to a patient are utilized in accessing an internal messaging system for viewing and/or sending care data for providing post procedure care to the user through a care network of the user. In the example of operation of the example system shown in FIG. 2, the user credentials management engine 208 updates user credentials in the user credentials datastore 210 to indicate user credentials assigned to the patient. Further, in the example of operation of the example system shown in FIG. 2, the user login engine 212 receives user credentials from the patient and logs in the patient based on the received user credentials. In the example of operation of the example system shown in FIG. 2, the post procedure care network management engine 214 functions to add a user to a care network of the patient based on instructions received from the patient. Additionally, in the example of operations of the example system shown in FIG. 2, the post procedure care network management engine 214 updates care network data stored in the care network datastore 216 to indicate that the user is part of the care network of the patient. In the example of operation of the example system shown in FIG. 2, the user credential management engine 208 sends an enrollment request to the user and assigns user credentials to the user. Further, in the example of operation, the user login engine 212 receives user credentials from the user and logs in the user with the received user credentials.

Figure 3:
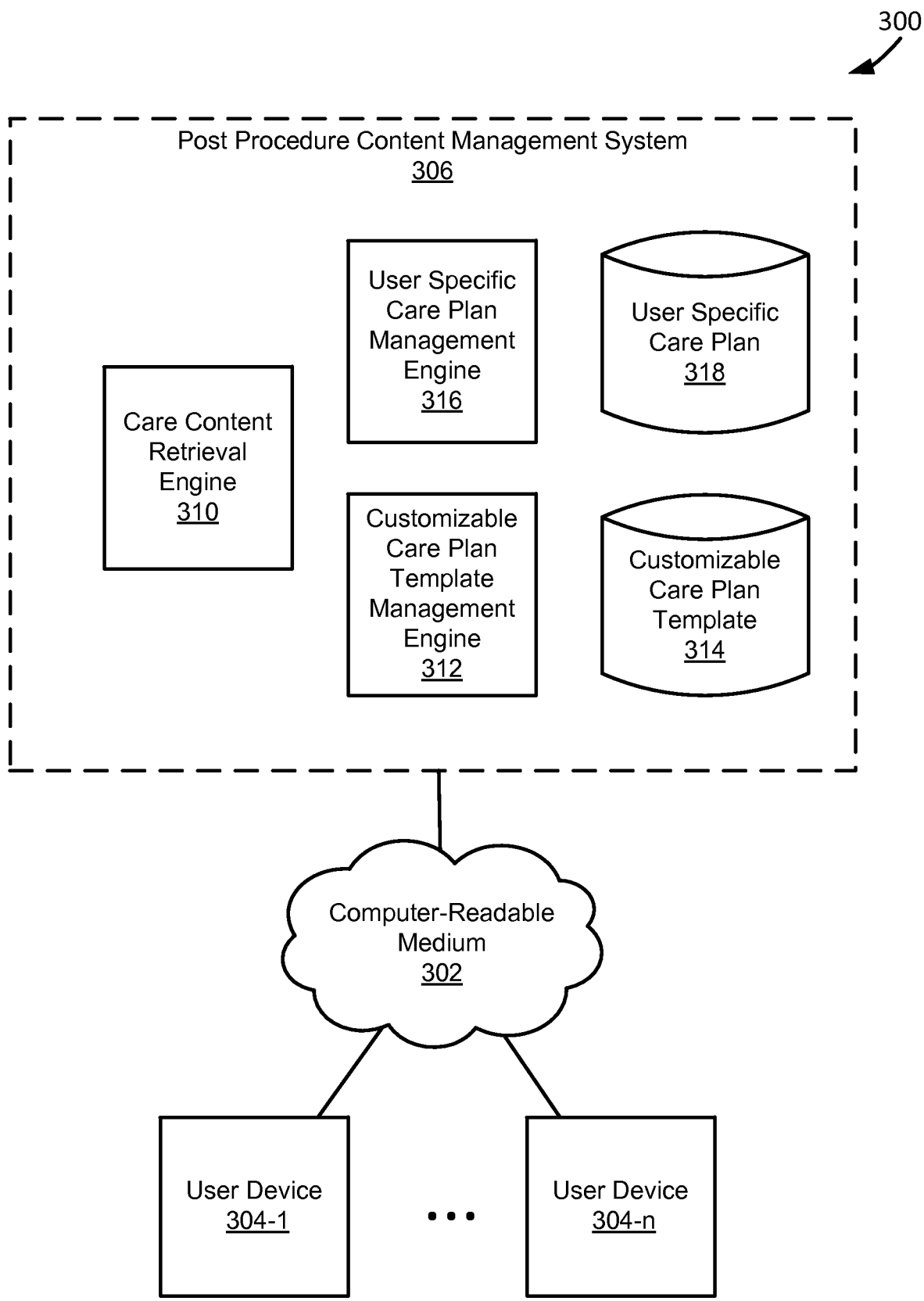
FIG. 3 depicts a diagram of an example of a system for managing post procedure content used in providing and/or maintaining post procedure care.

FIG. 3 depicts a diagram 300 of an example of a system for managing post procedure content used in providing and/or maintaining post procedure care. The example system shown in FIG. 3 includes a computer-readable medium 302, user devices 304-1 . . . 304-*n* (hereinafter referred to as "user devices 304"), and a post procedure content management system 306. In the example system shown in FIG. 3, the user devices 304 and the post procedure content management system 306 are coupled to each other through the computer-readable medium 302.

In a specific implementation, the user devices 304 function according to an applicable user device for sending and/or receiving data used in providing and/or maintaining post procedure care to a user through a care network of the user, such as the user devices described in this paper. The user devices 304 can be associated with a user who is the subject of a care network, and/or users within the care network of the user. The user devices 304 can be used to send care data including care content and post procedure care conditions for generating a user specific care plan. Depending upon implementation-specific or other considerations, the user devices 304 can be thin client devices or ultra-thin client devices. Further depending upon implementation-specific or other considerations, the user devices 304 can include wireless or cellular network interfaces through which the user devices 304 can be wirelessly connected to the computer-readable medium 302.

In a specific implementation, the post procedure content management system 306 functions to manage post procedure content used in providing and/or maintaining post procedure care for a user through a care network of the user. In managing post procedure content, the post procedure content management system 306 can retrieve care data including post procedure content and post procedure care conditions from either or both users within a care network and third party sources. For example, the post procedure content management system 308 can retrieve post procedure from a third party who provides standard care procedures. In another example, the post procedure content management system 308 can retrieve post procedure content and/or post procedure content conditions from a doctor who performed a procedure on a patient. Further, in managing post procedure content, the post procedure content management system 306 can generate a customizable care plan template. A customizable care plan template can include a template of a care plan that can be customized by a user, including either or both a care provider or a doctor who performed a procedure, to create a user specific care plan for a user upon whom a procedure was performed. The post procedure content management system can send a customizable care plan template to a user associated with the user devices 304. Additionally, the post procedure content management system can receive customized care plan data from a user within a care network. Customized care plan data can include post procedure content and/or post procedure care conditions generated either or both with the aid of a customizable care plan template and without the aid of a customizable care plan template. The post procedure content management system 306 can generate a user specific care plan from received customized care plan data.

In the example system shown in FIG. 3, the post procedure content management system includes a care content retrieval engine 310, a customizable care plan template management engine 312, a customizable care plan template datastore 314, a user specific care plan management engine 316, and a user specific care plan datastore 318. In a specific implementation, the care content retrieval engine 310 functions to retrieve care data, including post procedure content and/or post procedure care conditions. Depending upon implementation-specific or other considerations, the care content retrieval engine 310 can retrieve care data from either or both a third party source or users within a care network. For example, the care content retrieval engine 310 can retrieve care data from a third party source that provides standards for post procedure care. In another example, the care content retrieval engine 310 can retrieve care data from a doctor who performed a procedure on a patient.

In a specific implementation, the customizable care plan template management engine 312 functions to manage customizable care plan templates. In managing customizable care plan templates, the customizable care plan template management engine 312 can generate a customizable care plan template. Depending upon implementation-specific or other considerations, a customizable care plan template generated by the customizable care plan template management engine 312 can be specific to a type of procedure performed, a doctor who performs a procedure, and/or a caregiver. The customizable care plan template management engine 312 can generate a customized care plan template from care data retrieved by the care content retrieval engine 310. For example, the customizable care plan template management engine 312 can generate a customizable care plan template from care data retrieved from a third party source who provides standard care practices for a specific procedure. Further, in managing customizable care plan templates, the customizable care plan template management engine 312 can send a customizable care plan template to one or a plurality of users within a care network. For example, the customizable care plan template management engine 312 can send a customizable care plan template to a doctor who performed a procedure.

In a specific implementation, the customizable care plan template datastore 314 functions to store a customizable care plan. The customizable care plan template datastore 314 can store a customizable care plan template created by the customizable care plan template management engine 312. In sending a customizable care plan template to one or a plurality of user, the customizable care plan template management engine 312 can retrieve the customizable care plan template from the customizable care plan template datastore 314.

In a specific implementation, the user specific care plan management engine 316 functions to manage a user specific care plan for a user upon whom a procedure is performed. In managing a user specific care plan, the user specific care plan management engine 316 can generate a user specific care plan for a user. Depending upon implementation-specific or other considerations, the user specific care plan management engine 316 can generate a user specific care plan from received customized care plan data. Customized care plan data can be received, by the user specific care plan management engine 316, from a user within a care network in response to either a customizable care plan template or directly from a user without the aid of a customizable care plan template. Further depending upon implementation-specific or other considerations, the user specific care plan management engine 316 can generate a user specific care plan from care data retrieved by the care content retrieval engine 310.

In a specific implementation, the user specific care plan datastore 318 functions to store user specific care plan data. User specific care plan data includes data indicating a care plan for a user. User specific care plan data stored in the user specific care plan datastore 318 can indicate a user specific care plan for a user, as generated by the user specific care plan management engine 316. User specific care plan data stored in the user specific care plan datastore 318 can be stored as encrypted data at the file level, as in compliance with HIPAA standards. Further in compliance with HIPAA standards, the user specific care plan datastore 318 can be accessible through at least two factor authentication. For example, the user specific care plan datastore 318 can be accessed through an SSL VPN implementing at least two factor authentication.

In an example of operation of the example system shown in FIG. 3, the care content retrieval engine 310 retrieves care data. In the example of operation of the example system shown in FIG. 3, the customizable care plan template management engine 312 generates a customizable care plan template using, at least in part, the retrieved care data. Further, in the example of operation of the example system shown in FIG. 3, the customizable care plan template management engine 312 sends the customizable care plan template to a doctor within a care network. In the example of operation of the example system shown in FIG. 3, the user specific care plan management engine 316 receives customized care plan data from the doctor. Additionally, in the example of operation of the example system shown in FIG. 3, the user specific care plan management engine 316 generates a user specific care plan based on the received customized care plan data.

Figure 4:
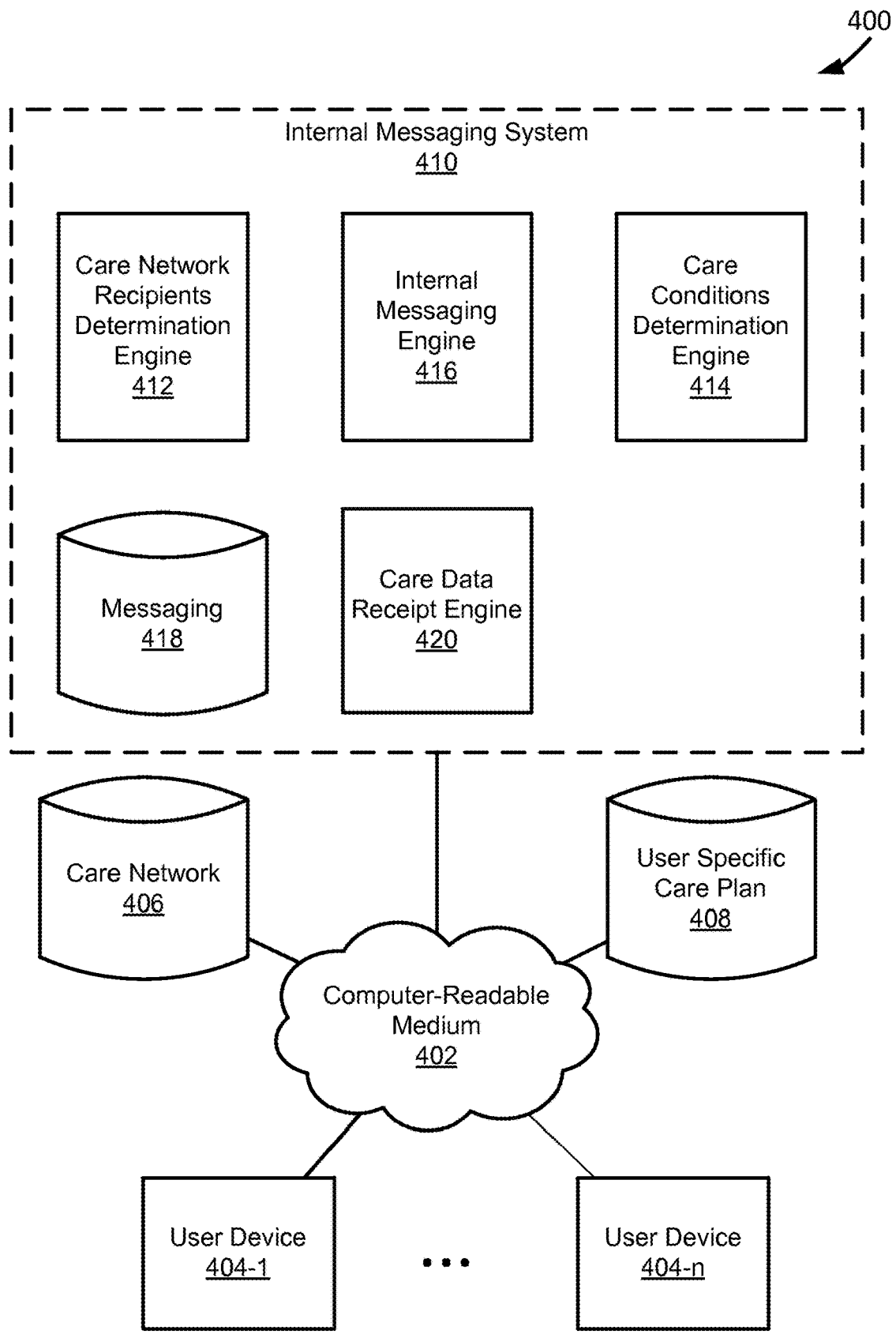
FIG. 4 depicts a diagram of an example of a system for sending messages internally between users in a care network in providing and/or maintaining post procedure care.

FIG. 4 depicts a diagram 400 of an example of a system for sending messages internally between users in a care network in providing and/or maintaining post procedure care. The example system shown in FIG. 4 includes a computer-readable medium 402, user devices 404-1 . . . 404-n (hereinafter referred to as "user devices 404"), a care network datastore 406, a user specific care plan datastore 408, and an internal messaging system 410. In the example system shown in FIG. 4, the user devices 404, the care network datastore 406, the user specific care plan datastore 408, and the internal messaging system 410 are coupled to each other through the computer-readable medium 402.

In a specific implementation, the user devices 404 function according to an applicable user device for sending and/or receiving data used in providing and/or maintaining post procedure care to a user through a care network of the user, such as the user devices described in this paper. The user devices 404 can be associated with a user who is the subject of a care network, and/or users within the care network of the user. The user devices 404 can be used to send and receive care data including care content and data generated in response to care data. Depending upon implementation-specific or other considerations, the user devices 404 can include applications that allow users to send and receive data for viewing care data and generating and sending care data through an internal messaging system. Depending upon implementation-specific or other considerations, the user devices 404 can be thin client devices or ultra-thin client devices. Further depending upon implementation-specific or other considerations, the user devices 404 can include wireless or cellular network interfaces through which the user devices 404 can be wirelessly connected to the computer-readable medium 402.

In a specific implementation, the care network datastore 406 functions according to an applicable datastore for storing care network data, such as the care network datastores described in this paper. Care network data stored in the care network datastore 406 can include data about a care network of a specific user. Depending upon implementation-specific or other considerations, care network data stored in the care network datastore 406 can include an identification of users within a care network, what care data can be sent to which users within the care network in accordance with satisfaction of post procedure care conditions for the care data, and/or external communication channels through which users can receive data.

In a specific implementation, the user specific care plan datastore 408 functions according to an applicable datastore for storing user specific care plan data, such as the user specific care plan datastores described in this paper. The user specific care plan datastore 408 can store user specific care plan data indicating a care plan for a user. User specific care plan data stored in the user specific care plan datastore 408 can include post procedure content that can be sent to users within a care network, and post procedure care conditions associated with sending the post procedure content.

In a specific implementation, the internal messaging system 410 functions according to an applicable system for transmitting data through internal communication channels to users within a care network for either or both providing post procedure care to a user and wellness to the user, such as the internal messaging systems described in this paper. The internal messaging system 410 can function to send and receive care data through internal communication channels to users within a care network. Depending upon implementation-specific or other considerations, the internal messaging system 410 can send post procedure content and receive/forward care data in response to the post procedure content. In sending care data through internal communication channels, the internal messaging system 410 can determine post procedure content to transmit according to care network data stored in the care network datastore 406 and user specific care plan data stored in the user specific care plan datastore 408. Additionally, in sending care data through internal communication channels, the internal messaging system 410 can determine post procedure care conditions for transmitting care data from care network data stored in the care network datastore 406 and user specific care plan data stored in the user specific care plan datastore 408.

In the example system shown in FIG. 4, the internal messaging system 410 includes a care network recipients determination engine 412, a care conditions determination engine 414, an internal messaging engine 416, a messaging datastore 418, and a care data receipt engine 420. In a specific implementation, the care network recipient determination engine 412 functions to determine care network recipients to care data to, in maintaining and/or providing post procedure care to a user through a care network of the user. The care network recipients determination engine 412 can determine recipients within a care network to receive care data using care network data stored in the care network datastore 406 and/or user specific care plan data stored in the user specific care plan datastore 408. Depending upon implementation-specific or other considerations, the care network recipients determination engine 412 can determine recipients of post procedure content. Further depending upon implementation-specific or other considerations, the care network recipient determination engine 412 can determine recipients of care data received by the internal messaging system 410. For example if measured vital statistics are received in response to a care alert, then the care network recipients determination engine 412 can determine recipients to which to transmit the received vital statistics.

In a specific implementation, the care conditions determination engine 414 functions to determine post procedure care conditions associated with sending of care content. The care conditions determination engine 414 can determine post procedure care conditions from user specific care plan data stored in the user specific care plan datastore 408. Depending upon implementation-specific or other considerations, the care conditions determination engine 414 can determine post procedure care conditions for transmitting post procedure content to users within a care network. Further depending upon implementation-specific or other considerations, the care conditions determination engine 414 can determine post procedure care conditions for transmitting received care data to users within a care network.

In a specific implementation, the internal messaging engine 416 functions to transmit care data in providing and/or maintaining post procedure care to a user through a care network of the user. The internal messaging engine 416 can transmit care data to recipients determined by the care network recipients determination engine 412 according to post procedure care conditions determine by the care conditions determination engine 414. Depending upon implementation-specific or other considerations, the internal messaging engine 416 can transmit care data directly to one or a plurality of users. For example, the internal messaging engine 416 can transmit care data directly to a plurality of users, thereby enabling group chat functionality. Further depending upon implementation-specific or other considerations, the internal messaging engine 416 can transmit care data by posting the care data to a feed that is viewable by one or a plurality of users within a care network. Depending upon implementation-specific or other considerations, a feed is viewable by a specific subset of users within a care network.

In a specific implementation, the internal messaging engine 416 functions to gain approval from a user before transmitting care data internally. Depending upon implementation-specific or other considerations, the internal messaging engine 416 can gain approval from a user before transmitting patient health information of the user. For example, the internal messaging engine 416 can gain approval for transmitting measured vital statistics of a user before transmitting the measured vital statistics. Further depending upon implementation-specific or other considerations, in gaining approval before transmitting care data internally, the internal messaging engine 416 can transmit internally a message to a user requesting approval to transmit the care data. Depending upon implementation-specific or other considerations, in gaining approval before transmitting care data internally, the internal messaging engine 416 can instruct an external messaging system to transmit a message through an external communication channel to a user requesting approval. In gaining approval before transmitting care data internally, the internal messaging engine 416 can be compliant with HIPAA standards.

In a specific implementation, the internal messaging engine 416 functions to transmit care data with different indicia or color coding schemes. Depending upon implementation-specific or other considerations, the internal messaging engine 416 can determine indicia or a color coding scheme in which to transmit care data based on an origination source of the care data, a recipient of the care data, the subject of care data, data included in care data, and/or post procedure care conditions. For example, if post procedure care conditions specify to call out care data sent to a doctor if a blood pressure reading included in care data is below a certain threshold, then the internal messaging engine 416 can mark a message sent to a doctor including the blood pressure reading with an exclamation point. In another example, the internal messaging engine 416 can mark all care data sent about a specific patient with a certain color.

In a specific implementation, the messaging datastore 418 functions to store messages and care data sent and/or received by the internal messaging system 410. Depending upon implementation-specific or other considerations, the messaging datastore 418 can store post procedure content sent by the internal messaging engine 416. Further depending upon implementation-specific or other considerations, the messaging datastore 418 can store care data received by the internal messaging system 410. The messaging datastore 418 can store transmission records of data sent and received by the internal messaging system. Transmission records can include a source of care data, a recipient of care data transmitted by the internal messaging system, and/or a time when the care data was sent and/or received. Data stored in the messaging datastore 418 can be stored as encrypted data at the file level, as in compliance with HIPAA standards. Further in compliance with HIPAA standards, the messaging datastore 418 can be accessible through at least two factor authentication. For example, the messaging datastore 418 can be accessed through an SSL VPN implementing at least two factor authentication. Depending upon implementation-specific or other configurations, the messaging datastore 418 can be configured to not allow users to delete data from the messaging datastore 418, in compliance with HIPAA standards. For example, users can be restricted in deleting messages they receive through the internal messaging system 410. Further depending upon implementation, specific or other considerations, data stored in the messaging datastore 418 is backed up and saved for at least 6 years, further in compliance with HIPAA standards.

In a specific implementation, the care data receipt engine 420 functions to receive care data from users within a care network in providing and/or maintaining post procedure care. The care data receipt engine 420 can receive care data from users within a care network in response to post procedure care content. The care data receipt engine 420 can provide received care data to the internal messaging engine 416, where the received data can be transmitted in accordance with post procedure care conditions to appropriate recipients within a care network.

In an example of operation of the example system shown in FIG. 4, the care network recipients determination engine 412 determines recipients within a care network for receiving care data. In the example of operation of the example system shown in FIG. 4, the care conditions determination engine determines post procedure care conditions for sending the care data. Further, in the example of operation of the example system shown in FIG. 4, the internal messaging engine 416 sends the care data to the recipients according the post procedure care conditions. In the example of operation of the example system shown in FIG. 4, the messaging datastore 418 stores the transmitted care data. Additionally, in the example of operation of the example system shown in FIG. 4, the care data receipt engine 420 receives care data in response to the transmitted care data. In the example of operation of the example system shown in FIG. 4, the internal messaging engine 416 transmits the care data received by the care data receipt engine 420 to appropriate recipients within the care network according to post procedure care conditions.

Figure 5:
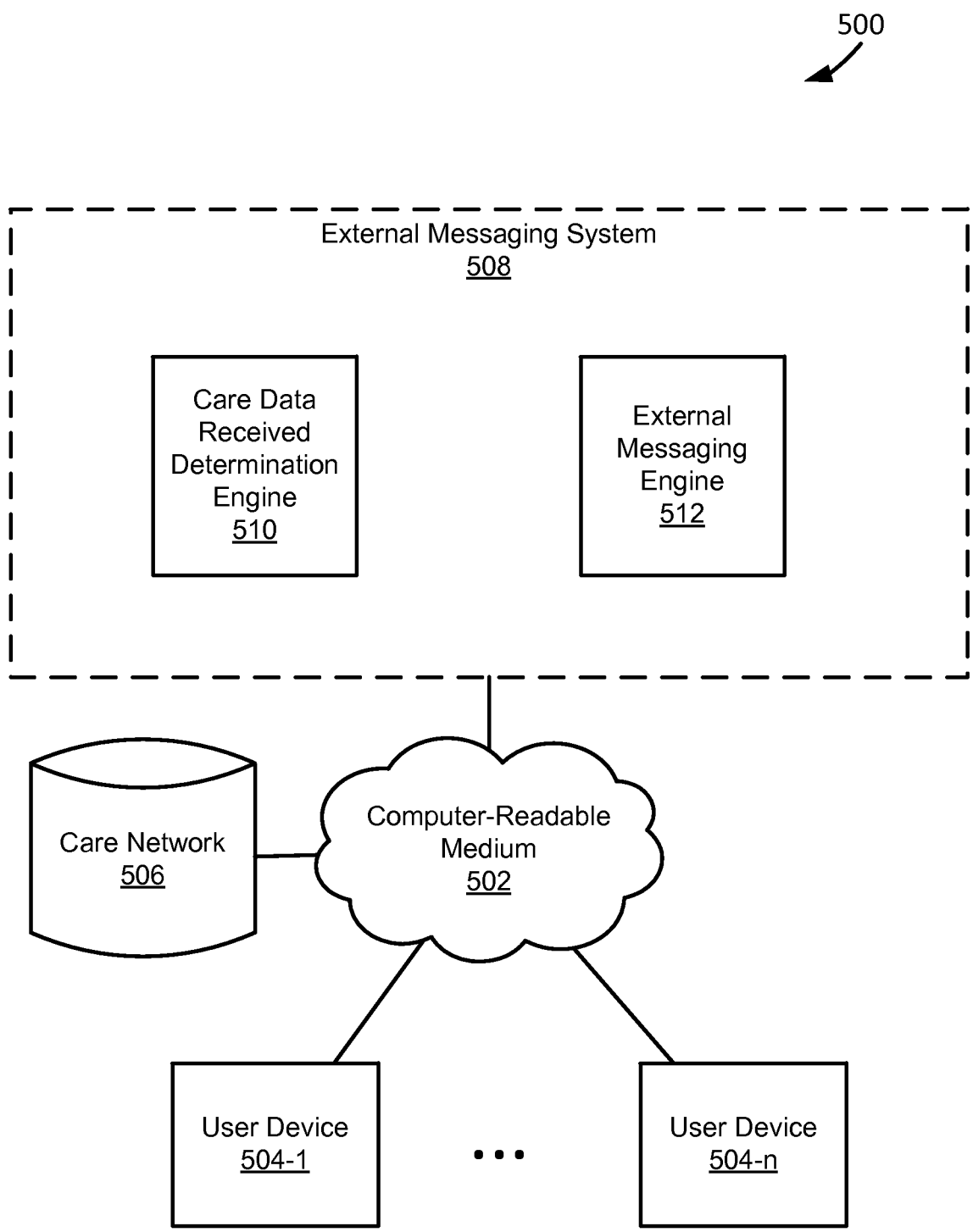
FIG. 5 depicts a diagram of an example of an external messaging system for providing and/or maintaining post procedure care for a user through a care network of the user.

FIG. 5 depicts a diagram 500 of an example of an external messaging system for providing and/or maintaining post procedure care for a user through a care network of the user. The example system shown in FIG. 5 includes a computer-readable medium 502, user device 504-1 . . . 504-n (hereinafter referred to as "user devices 504"), a care network datastore 506, and an external messaging system 508. In the example system shown in FIG. 5, the user devices 504, the care network datastore 506, and the external messaging system 508 are coupled to each other through the computer-readable medium 502.

In a specific implementation, the user devices 504 function according to an applicable user device for sending and/or receiving data used in providing and/or maintaining post procedure care to a user through a care network of the user, such as the user devices described in this paper. The user devices 504 can be associated with a user who is the subject of a care network, and/or users within the care network of the user. The user devices 504 can be used to receive care data received notifications. Depending upon implementation-specific or other considerations, the user devices 504 can be thin client devices or ultra-thin client devices. Further depending upon implementation-specific or other considerations, the user devices 504 can include wireless or cellular network interfaces through which the user devices 504 can be wirelessly connected to the computer-readable medium 502.

In a specific implementation, the care network datastore 506 functions according to an applicable datastore for storing care network data, such as the care network datastores described in this paper. Care network data stored in the care network datastore 506 can include data about a care network of a specific user. Depending upon implementation-specific or other considerations, care network data stored in the care network datastore 506 can include an identification of users within a care network, what care data can be sent to which users within the care network in accordance with satisfaction of post procedure care conditions for the care data, and/or external communication channels through which users can receive data.

In a specific implementation, the external messaging system 508 functions to send messages through an external communication channel to users within a care network for providing and/or maintaining post procedure care to a user. The external messaging system 508 can send care data received notifications. In sending messages through an external communication channel, the external messaging system 508 can determine whether an account associated with a user has received care data through an internal messaging system. Further, the external messaging system 508 can determine external communication channels to send messages to users through, and subsequently send messages through the determined external communication channels to the users.

In the example system shown in FIG. 5, the external messaging system 508 includes a care data received determination engine 510 and an external messaging engine 512. In a specific implementation, the care data received determination engine 510 functions to determine if an account has received care data through an internal messaging system. Depending upon implementation-specific or other considerations, the care data received determination engine 510 can determine if an account has received care data through an internal messaging system in real time as the care data is sent to the account. Further depending upon implementation-specific or other considerations, the care data received determination engine 510 can determined an account has received care data based on a notification from the internal messaging system. The care data received determination engine can determine a user associated with an account through care network data stored in the care network datastore 506.

In a specific implementation, the external messaging engine 512 functions to send a notification over an external communication channel indicating that the user has received care data through an internal messaging system. The external messaging engine 512 can send care data received notifications based on a determination of a user associated with an account that has received care data through an internal messaging system, as determined by the care data received determination engine 510. Depending upon implementation-specific or other considerations, the external messaging engine 512 can determine a preferred external communication channel from care network data stored in the care network datastore 506 and subsequently send notification to the users over the preferred external communication channels. Examples of external communication channels through which the external messaging engine 512 can send notifications are text and/or email. Notifications sent by the external messaging engine are generic in that they do not contain any patient health information and are therefore in compliance with HIPAA.

In an example of operation of the example system shown in FIG. 5, the care data received determination engine 510 determines a user associated with an account that has received care data through an internal communication system. In the example of operation of the example system shown in FIG. 5, the external messaging engine 512 determines a preferred communication channel of the user determined by the care data received determination engine 510. Further, in the example of operation of the example system shown in FIG. 5, the external messaging engine 512 sends a care data received notification to the user through the preferred communication channel of the user.

Figure 6:
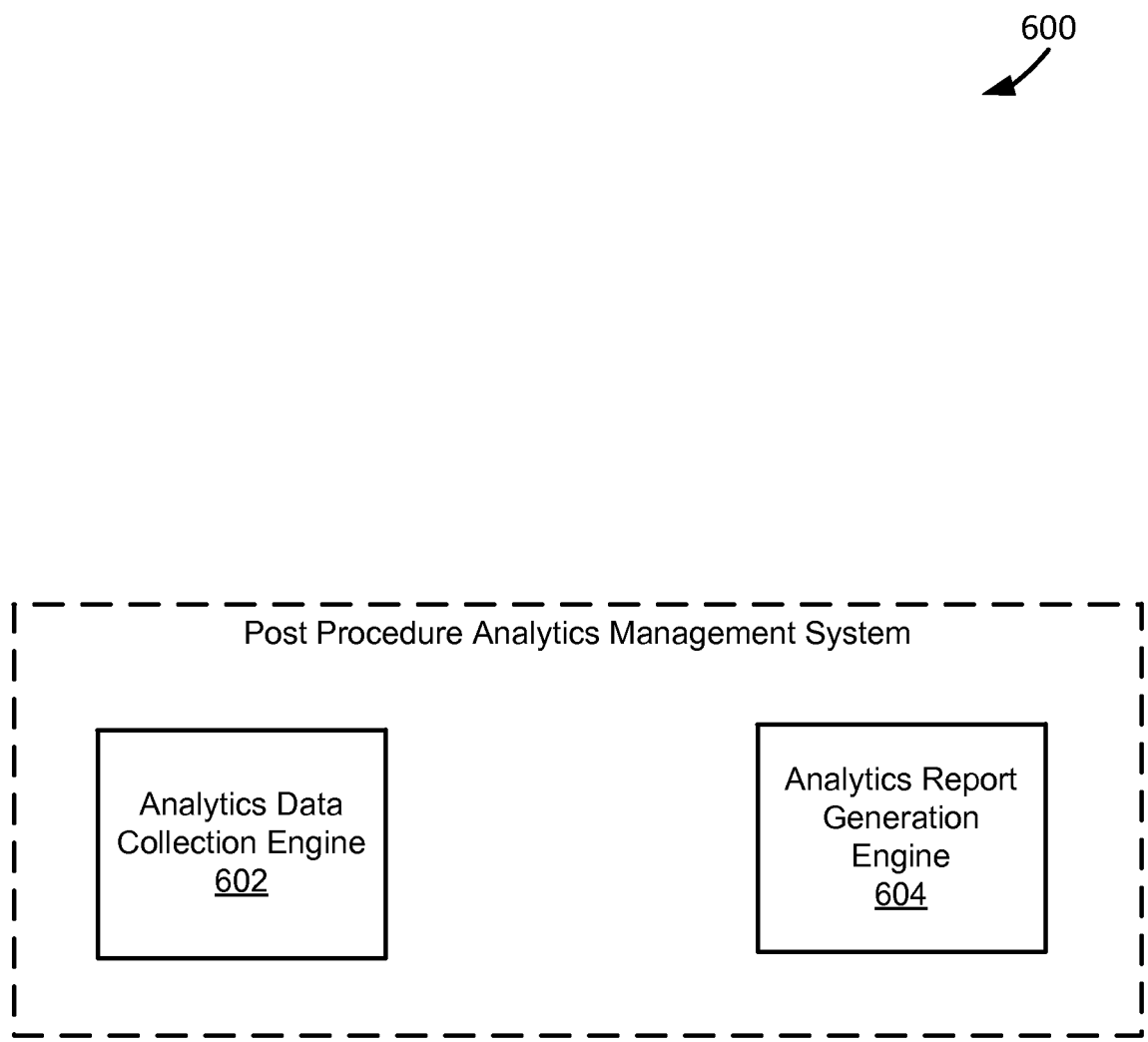
FIG. 6 depicts a diagram of a post procedure analytics management system.

FIG. 6 depicts a diagram 600 of a post procedure analytics management system. The example system shown in FIG. 6 includes an analytics data collection engine 602 and an analytics report generation engine 604.

In a specific implementation, the analytics data collection engine 602 functions to collect analytics data based on providing and/or maintaining post procedure care to a user through a care network. Analytics data can include actions that are taken by users in a care network in providing post procedure care, usage analytics of users in a care network, and/or care analytics of providing post procedure care to a user through a care network. Care analytics can include the type of care data that was transmitted internally, which users provided care data, and/or which user received care data.

In a specific implementation, the analytics report generation engine 604 functions to generate an analytics report based on analytics data collected by the analytics data collection engine 602. The analytics report generation engine 604 can generate an analytics report for each type of analytics data or a report with combined different types of analytics data. Depending upon implementation-specific or other considerations, the analytics report generation engine 604 can send the analytics report to users within a care network, or otherwise make the analytics report viewable to eth users within the care network. Users within a care network can use an analytics report to improve post procedure care and/or provide coaching to users within the care network.

Figure 7:
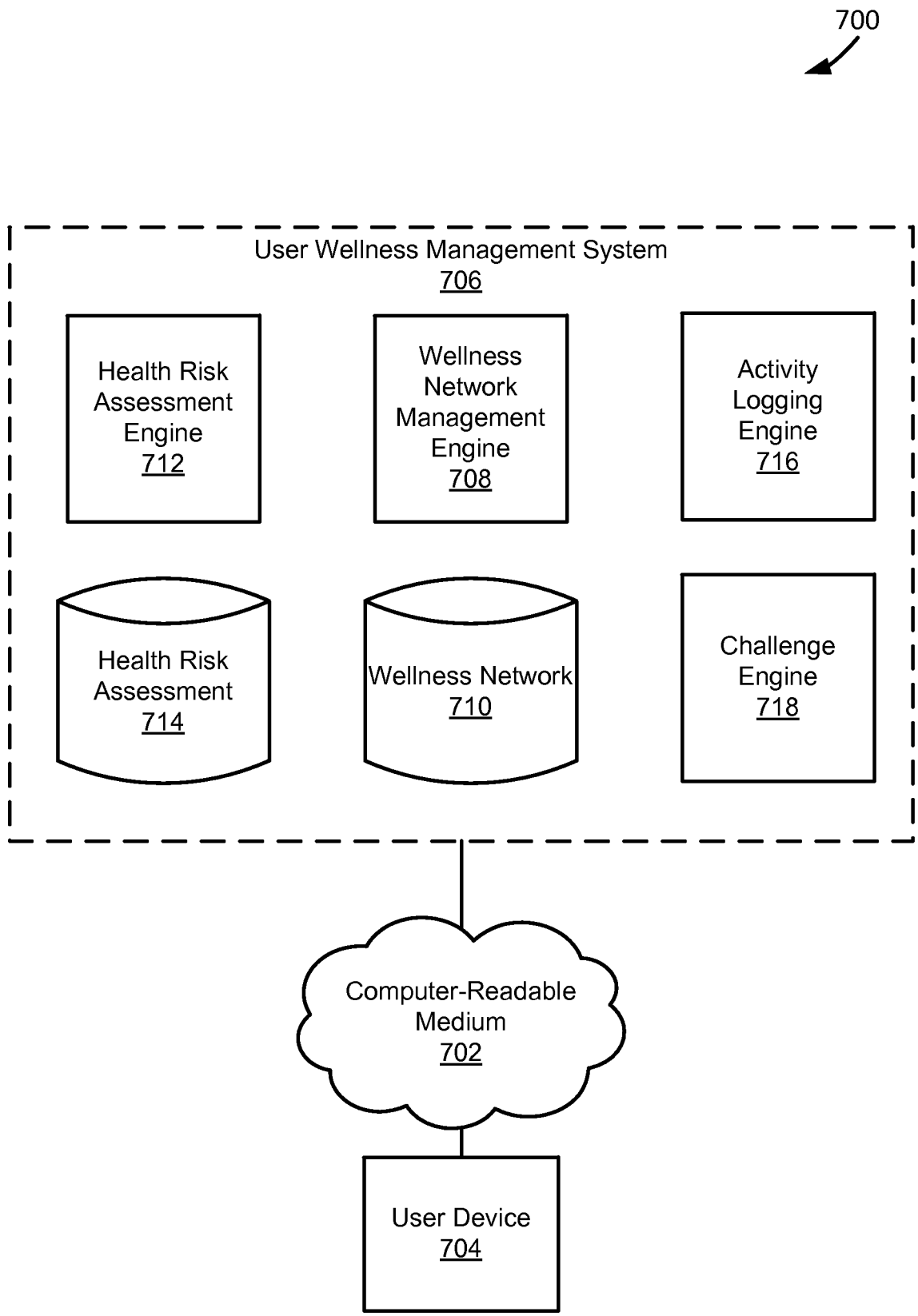
FIG. 7 depicts a diagram of an example of a system for sending messages internally between users in a care network in providing and/or maintaining post procedure care.

FIG. 7 depicts a diagram 700 of an example of a system for sending messages internally between users in a care network in providing and/or maintaining post procedure care. The example system shown in FIG. 7 includes a computer-readable medium 702, a user device 704, and a user wellness management system 706. In the example system shown in FIG. 7, the user device 704 and the user wellness management system 706 are coupled to each other through the computer-readable medium 702.

In a specific implementation, the user device 704 functions according to an applicable device for sending and receiving wellness data used in providing wellness to a user through a wellness network, such as the user devices described in this paper. The user device 704 can send and receive data to and from the user wellness management system through an applicable system for sending and receiving data through internal communication channels, such as the internal messaging systems described in this paper.

In a specific implementation, the user wellness management system 706 functions to provide wellness to a user through a wellness network. A wellness network can include a plurality of users that are chosen by a user who is the subject of the wellness network. Depending upon implementation-specific or other considerations, the user wellness management system 706 can perform a health risk assessment of a user. Further depending upon implementation-specific or other considerations, the user wellness management system 706 can track activities of a user and challenge the user to perform certain activities to improve the wellness of the user.

In the example system shown in FIG. 7, the user wellness management system 706 includes a wellness network management engine 708, a wellness network datastore 710, a health risk assessment engine 712, a health risk assessment datastore 714, an activity logging engine 716, and a challenge engine 718. In a specific implementation, the wellness network management engine 708 functions to manage a wellness of a user. In managing a wellness network of a user, the wellness network management engine 708 can add and/or remove users from a wellness network. Example of users that can be in a wellness network include family members and/or lifestyle coaches. Users within a wellness network can communication through an applicable internal messaging system, such as the internal messaging systems described in this paper.

In a specific implementation, the wellness network datastore 710 functions to store wellness network data indicating a wellness network of a user. Wellness network data can indicate users within a wellness network and ways in which the users can be contacted. Wellness network data stored in the wellness network datastore 710 can be generated and/or modified by the wellness network management engine 708. Wellness network data stored in the wellness network datastore 710 can be stored as encrypted data at the file level, as in compliance with HIPAA standards. Further in compliance with HIPAA standards, the wellness network datastore 710 can be accessible through at least two factor authentication. For example, the wellness network datastore 710 can be accessed through an SSL VPN implementing at least two factor authentication.

In a specific implementation, the health risk assessment engine 712 functions to perform a health risk assessment on a user who is the subject of a wellness network. A health risk assessment can include potential health risks to a user. The health risk assessment engine 712 can perform a health risk by presenting questions and based on a user's answer to those questions, generate a health risk assessment. Examples of questions that the health risk assessment engine 712 can present to a user include, how often a user exercises, what a user's diet includes, and whether a user smokes. The health risk assessment engine 712 can store a health risk assessment for a user as health risk assessment data in the health risk assessment datastore 714. Depending upon implementation-specific or other considerations, the health risk assessment engine 712 can perform a health risk assessment on a user, once or a plurality of times throughout the life of a user.

In a specific implementation, the activity logging engine 716 functions to log activities of a user in providing wellness to a user. The activity logging engine 716 can log activities related to diet, exercise, and daily occurrences of a user. Depending upon implementation-specific or other considerations, the activity logging engine 716 can determine activities to log by asking questions for a user. For example, the activity logging engine 716 can ask a user if they exercised on a specific day. Further depending upon implementation-specific or other considerations, the activity logging engine 716 can determine activities to log from data received from a wearable device of a user, an application, and/or a service, such as the wearable devices, applications, and services previously described. Depending upon implementation-specific or other considerations, the activity logging engine 716 can generate a wellness report of logged activities that a user can view to improve their wellness. Further depending upon implementation-specific or other considerations, wellness points can be awarded based on the performance of certain activities logged by the activity logging engine 716. Wellness points can be used to redeem gifts or obtain rewards, e.g. a gift card.

In a specific implementation, the challenge engine 718 functions to present challenges to a user, that the user can perform to improve their wellness. Depending upon implementation-specific or other considerations, the challenge engine 718 can present challenges based on specific health risks to a user, as identified in a health risk assessment. Further depending upon implementation-specific or other considerations, the challenge engine 718 can present a challenge created by another user, e.g. a wellness coach. Challenges can include associated wellness points that can be awarded to a user after completion of a challenge or a portion of a challenge.

In an example of operation of the example system shown in FIG. 7, the wellness network management engine 708 manages a wellness network of a user. In the example of operation of the example system shown in FIG. 7, the health risk assessment engine generates a health risk assessment for the user. Further, in the example of operation of the example system shown in FIG. 7, the activity logging engine logs activities of a user for use in monitoring wellness of the user. In the example of operation of the example system shown in FIG. 7, the challenge engine 718 presents challenges to the user that can improve the wellness of the user if they are performed.

Figure 8:
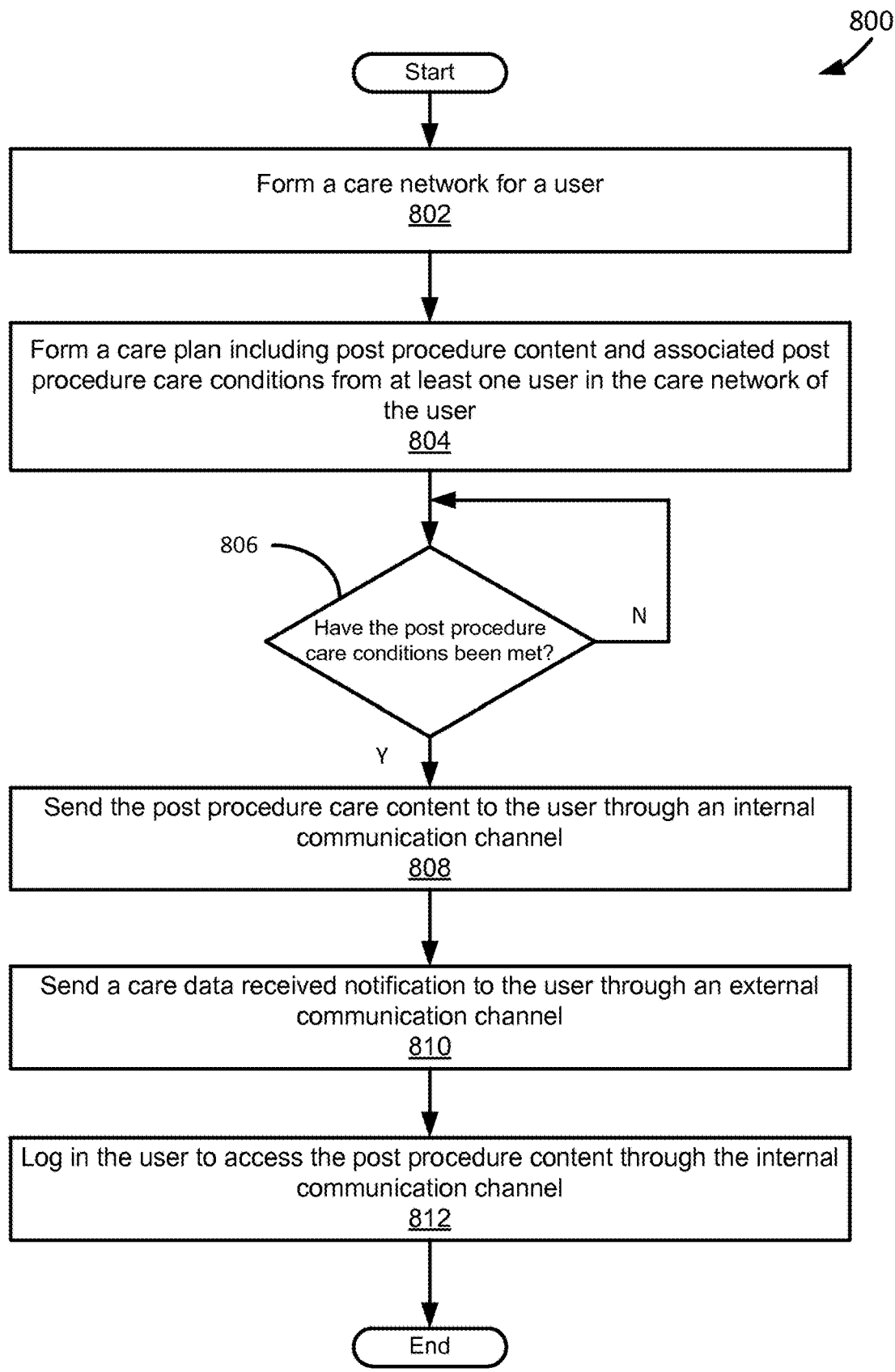
FIG. 8 depicts a flowchart of an example of a method for providing and/or maintaining post procedure care to a user through a care network of the user.

FIG. 8 depicts a flowchart 800 of an example of a method for providing and/or maintaining post procedure care to a user through a care network of the user. The flowchart 802 begins at module 802, where a care network of a user is formed. A care network of a user can include family members who will provide care to a user and/or doctors who performed a procedure on the user. A care network of a user can be formed by a post procedure care network management engine.

The flowchart 800 continues to module 804 where a care plan is formed for a user. A care plan can include post procedure content to send to the user or other users within the care network and post procedure care conditions that must be met in order to send the post procedure care content. Depending upon implementation-specific or other considerations, post procedure content included in the care plan can include care alerts. Further depending upon implementation-specific or other considerations, the care plan can be formed either with or without the aid of a customizable care plan template. The care plan can be formed by a user specific care plan management engine.

The flowchart 800 continues to decision point 806 where it is determined if the post procedure care conditions have been met. If it is determined that the post procedure care conditions are met, then the flowchart 800 continues to module 808. At module 808, the post procedure care content is sent to the user through an internal communication channel. An internal messaging engine can send the post procedure content through an internal communication channel. Depending upon implementation-specific or other considerations, the post procedure content can be sent directly to an account associated with the user or posted on a feed that the user can view.

The flowchart 800 continues to module 810, where a care data received notification is sent to the user through an external communication channel. Depending upon implementation-specific or other considerations, an external communication channel can be a preferred external communication channel of the user. An external messaging engine can send the care data received notification to the user through an external communication channel. A care data received notification sent through the external communication channel can be generic in that it does not contain any personal health information of the user.

The flowchart 800 continues to module 812, where the user is logged in to access the post procedure content sent through the internal communication channel. In logging in the user, user credentials for the user can be received and then authenticated in order to login the user. Depending upon implementation-specific or other considerations, the user can remain logged in until a certain period of inactivity occurs, after which the user will be logged out. A user login engine can manage the logging in and logging out of the user.

Figure 9:
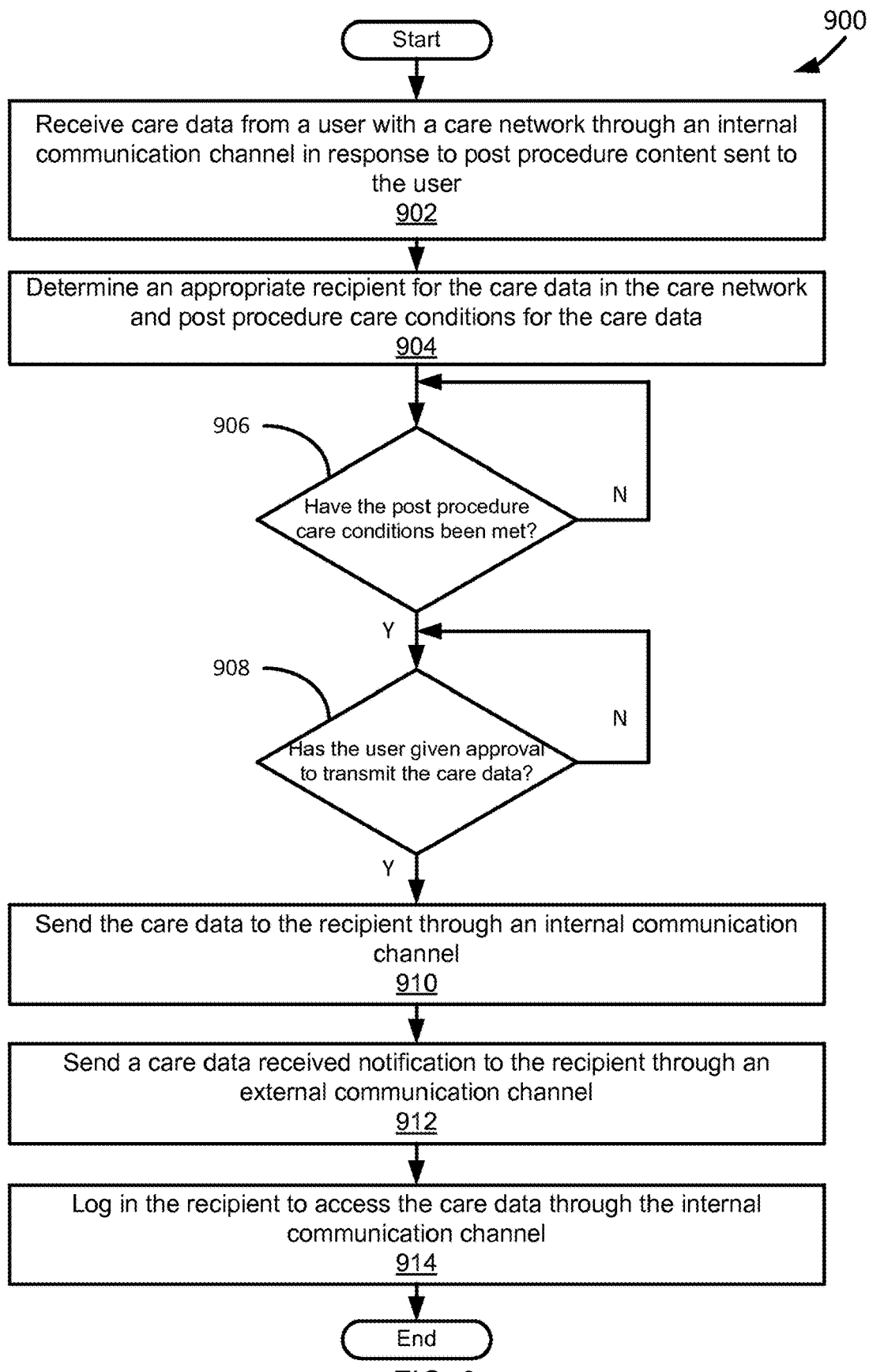
FIG. 9 depicts a flowchart of an example of a method for sending care data in a care network of a user for providing and/or maintaining post procedure care to the user through the care network of the user.

FIG. 9 depicts a flowchart 900 of an example of a method for sending care data in a care network of a user for providing and/or maintaining post procedure care to the user through the care network of the user. The flowchart 900 begins at module 902, where care data is received from a user with a care network through an internal communication channel. Care data received at module 902 can be generated in response to post procedure content sent to the user. For example, care data can be measured vital statistics of the user in response to post procedure content that is a care alert reminding the user to take their vital statistics. The care data can be received by a care data receipt engine.

The flowchart 900 continues to module 904, where an appropriate recipient for the care data in the care network is determined. An appropriate recipient for the care data can be determined by a care network recipients determination engine. An appropriate recipient can be determined based on care network data for the care network and/or user specific care plan data for the user. Additionally, at module 904, post procedure care conditions can be determined for the care data. Post procedure care conditions can be determined by a care conditions determination engine.

The flowchart 900 continues to decision point 906, where it is determined whether the post procedure care conditions are met. If it is determined that the post procedure care conditions are met, then the flowchart 900 continues to decision point 908. At decision point 908 it is determined whether the user has given approval to transmit the care data.

If it is determined that the user has given approval to transmit the care data, then the flowchart 900 continues to module 910. At module 910, the care data is sent to the recipient through an internal communication channel. An internal messaging engine can send the care data through an internal communication channel. Depending upon implementation-specific or other considerations, the care data can be sent directly to an account associated with the recipient or posted on a feed that the recipient can view.

The flowchart 900 continues to module 912, where a care data received notification is sent to the recipient through an external communication channel. Depending upon implementation-specific or other considerations, an external communication channel can be a preferred external communication channel of the recipient. An external messaging engine can send the care data received notification to the recipient through an external communication channel. A care data received notification sent through the external communication channel can be generic in that it does not contain any personal health information of the recipient.

The flowchart 900 continues to module 912, where the recipient is logged in to access the care data sent through the internal communication channel. In logging in the recipient, user credentials for the recipient can be received and then authenticated in order to login the recipient. Depending upon implementation-specific or other considerations, the recipient can remain logged in until a certain period of inactivity occurs, after which the recipient will be logged out. A user login engine can manage the logging in and logging out of the recipient.

Figure 10:
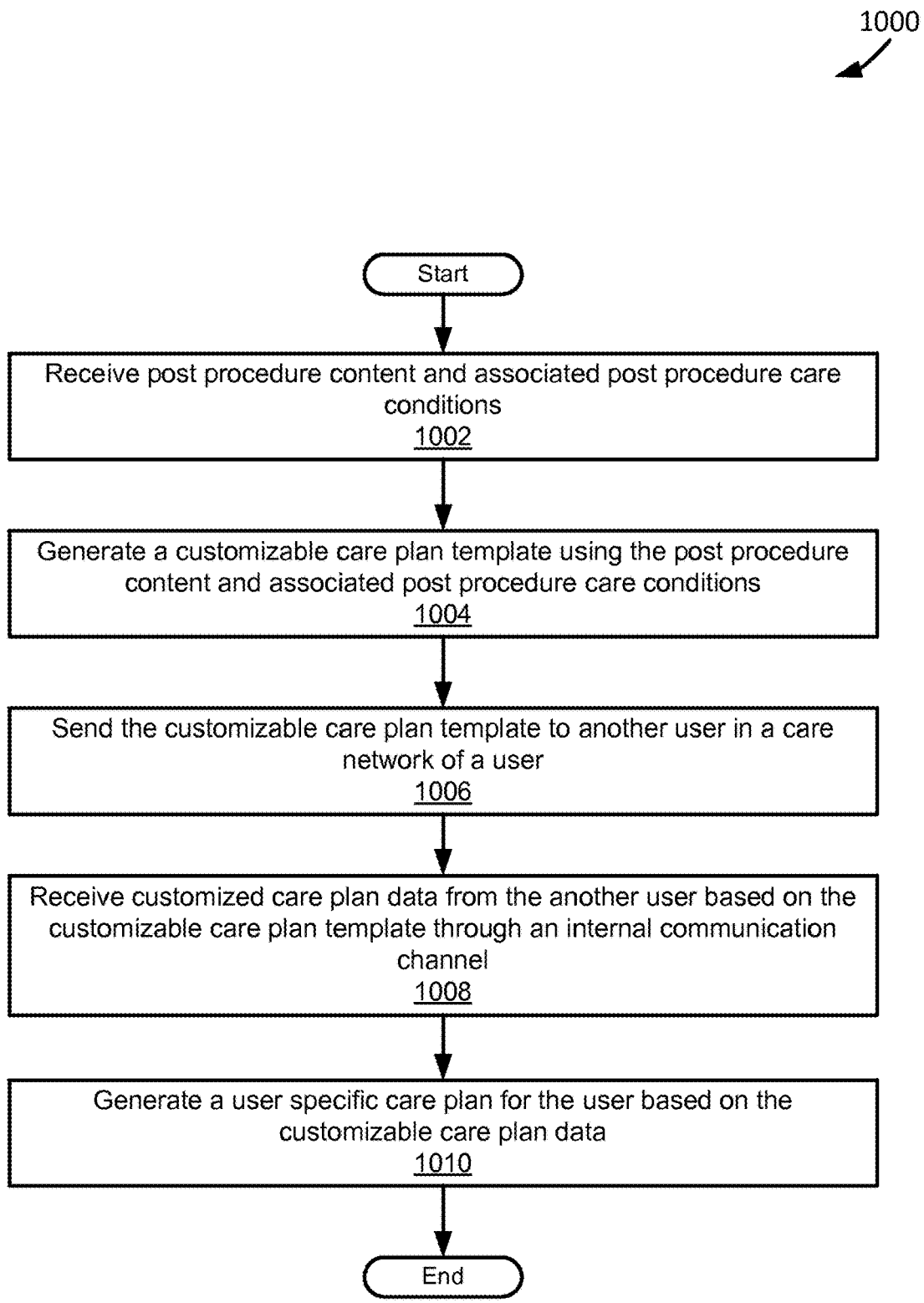
FIG. 10 depicts a flowchart of an example of a method for generating a user specific care plan for providing and/or maintaining post procedure care of a user through a care network of the user.

FIG. 10 depicts a flowchart 1000 of an example of a method for generating a user specific care plan for providing and/or maintaining post procedure care of a user through a care network of the user. The flowchart 1000 begins at module 1002 where post procedure content and associated post procedure conditions are received. Post procedure content and associated post procedure conditions can be received by a care content retrieval engine. Depending upon implementation-specific or other considerations, post procedure content and associated post procedure conditions can be received from a third party source, a care provider, and/or a doctor who performed the procedure.

The flowchart 1000 continues to module 1004 where a customizable care plan template is generating using the post procedure content and associated post procedure care conditions. A customizable care plan template can be specific to a type of procedure and/or a doctor who performed a procedure. A customizable care plan template can be generated by a customizable care plan template management engine.

The flowchart 1000 continues to module 1006 where the customizable care pan template is sent to a user in a care network of the user. The another user in the care network of the user can be a doctor who performed the procedure and/or a care giver. The customizable care plan template can be sent through an internal communication channel by the customizable care plan template management engine.

The flowchart 1000 continues to module 1008 where customized care plan data is received from the another user based on the customizable care plan template. The customized care plan data can be received through an internal communication channel. A user specific care plan management engine can receive the customized care plan data.

The flowchart 1000 continues to module 1010 where a user specific care plan is generated for the user based on the customized care plan data. A user specific care plan management engine can generate the user specific care plan. A user specific care plan can include care data, including post procedure content and associated post procedure care conditions, for providing and/or maintaining post procedure care to the user.

Figure 11:
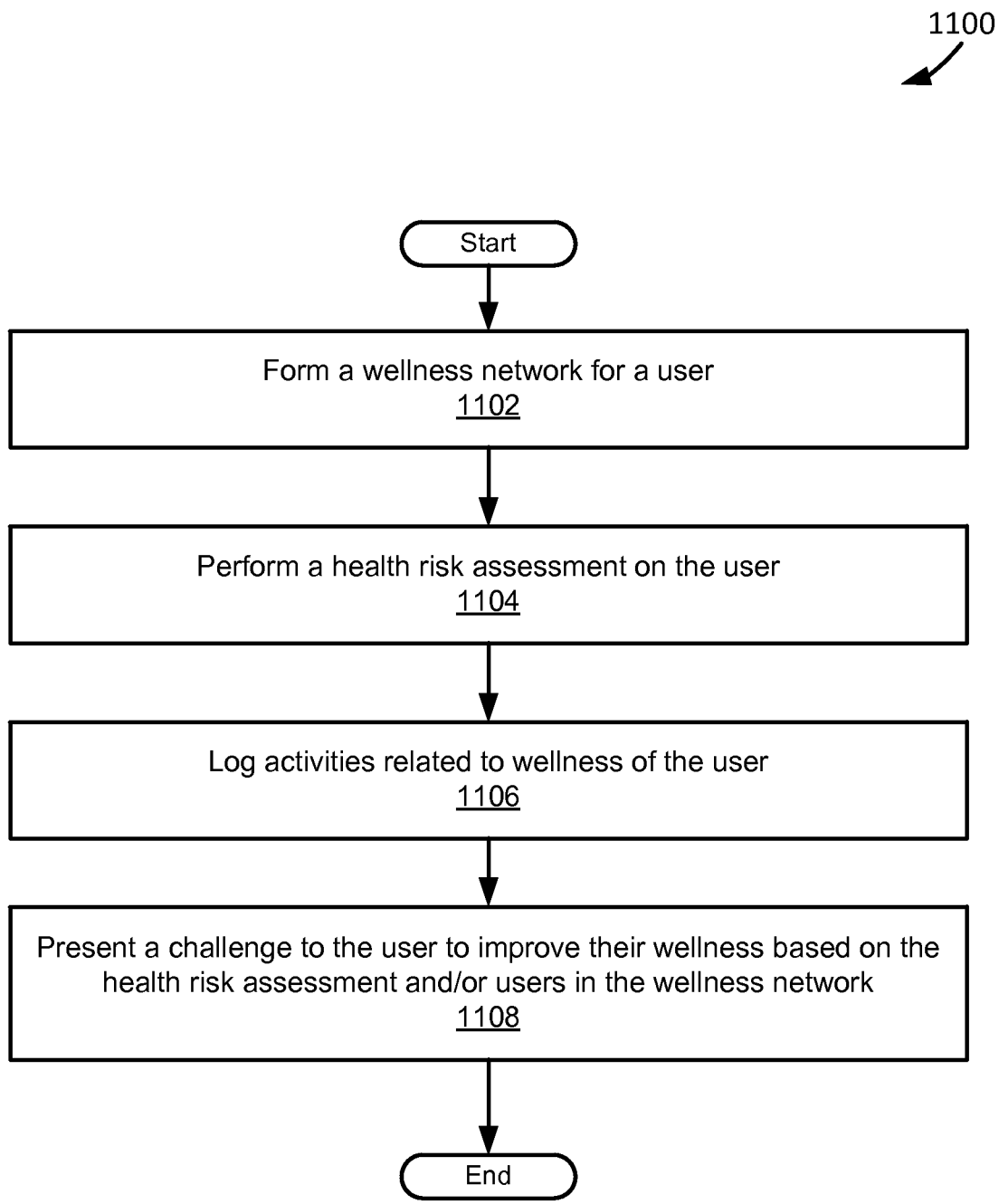
FIG. 11 depicts a flowchart of an example of a method for providing and/or maintaining wellness for a user.

FIG. 11 depicts a flowchart 1100 of an example of a method for providing and/or maintaining wellness for a user. The flowchart 1100 begins at module 1102 where a wellness network is formed for a user. A wellness network can include family members and coaches for promoting wellness for a user. A wellness network management engine can form a wellness network for a user based on instructions received from the user indicating parties that the user wants in their wellness network.

The flowchart 1100 continues to module 1104 where a health risk assessment is performed for the user. A health risk assessment can be performed by presenting questions to the user and forming the assessment based on the answers to the questions provided by the user. A health risk assessment can be performed by a health risk assessment engine.

The flowchart 1100 continues to module 1106 where activities related to the wellness of the user are logged. Activities related to the wellness of the user can include exercise activities and dietary activities. An activity logging engine can log the activities related to the wellness of the user. Depending upon implementation-specific or other considerations, the log of the activities can be presented to a user for coaching the user in wellness.

The flowchart 1100 continues to module 1108, where a challenge is presented to the user to improve their wellness based on the health risk assessment and/or users in the wellness network. For example, a coach in the wellness network can suggest a challenge that a user should undertake. In another example, a challenge that a user should undertake can be determined based on particular health risks of the user indicated by the health risk assessment.

Figure 12:
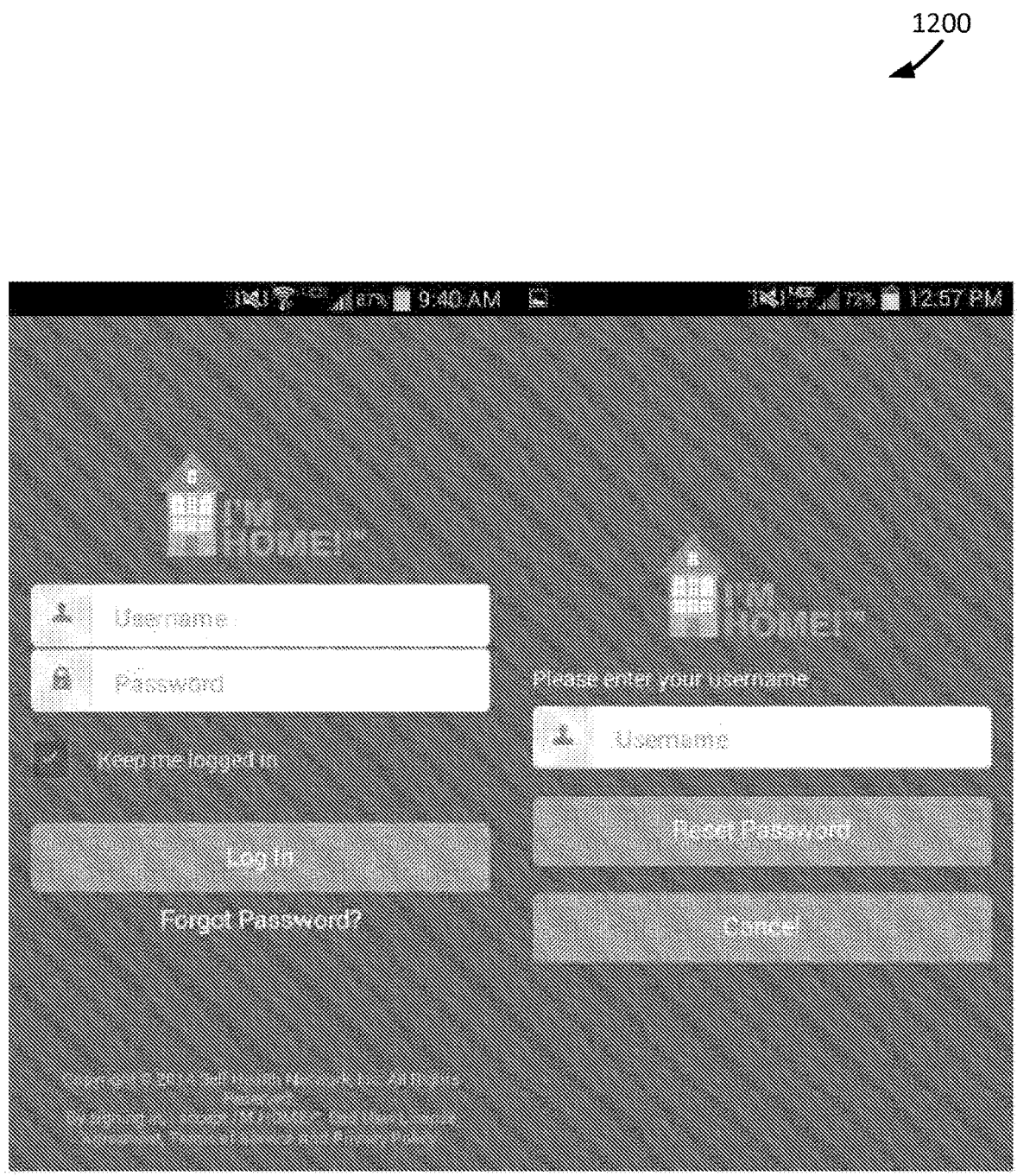
FIG. 12 depicts an example of a screenshot of an interface used to log in to an internal communication channel.

FIG. 12 depicts an example of a screenshot 1200 of an interface used to log in to an internal communication channel. The interface includes fields in which user credentials can be entered and used to access care data sent through an internal messaging system.

Figure 13:
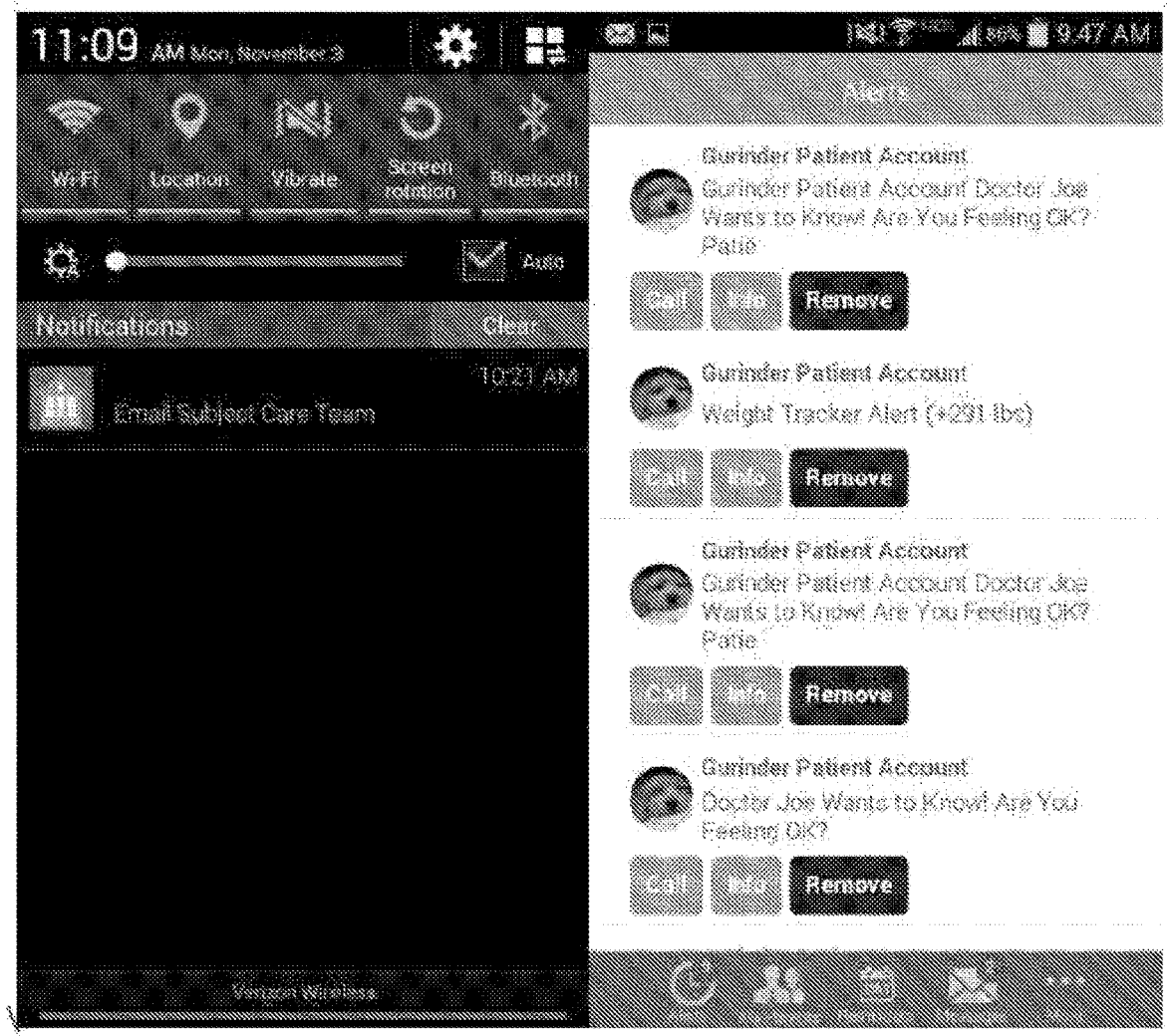
FIG. 13 depicts an example of a screenshot of an interface for use in managing post procedure care of users in care networks.

FIG. 13 depicts an example of a screenshot 1300 of an interface for use in managing post procedure care of users in care networks. The interface includes tabs through which a user can view info about users within a care network. The interface also includes tabs through which a user can activate to transmit care data used in managing and/or providing post procedure care data to a user.

Figure 14:
FIG. 14 depicts an example of a screenshot of another example of an interface for use in managing post procedure care of users in care networks.

FIG. 14 depicts an example of a screenshot 1400 of another example of an interface for use in managing post procedure care of users in care networks. The interface includes contact information of patient. The interface also includes messages including care data sent to the patients.

These and other examples provided in this paper are intended to illustrate but not necessarily to limit the described implementation. As used herein, the term "implementation" means an implementation that serves to illustrate by way of example but not limitation. The techniques described in the preceding text and figures can be mixed and matched as circumstances demand to produce alternative implementations.

We claim:

1. A computer-implemented method comprising:
   generating a care network for a care recipient in providing post procedure care to the care recipient for a procedure performed on the care recipient;
   generating a user specific care plan for the care recipient, the user specific care plan including post procedure content and first post procedure care conditions associated with the post procedure content;
   determining if the first post procedure care conditions are satisfied;
   if it is determined that the first post procedure care conditions are satisfied:
      sending the post procedure content to the care recipient through an internal communication channel;
      sending a first care data received notification to the care recipient through an external communication channel that is separate from the internal communication channel and includes at least one of a short message service communication channel, an email communication channel, and a push notification communication channel, the first care data received notification being a generic notification lacking any personal health information of the care recipient and indicating that the care recipient has received the post procedure content through the internal communication channel, wherein the first care data received notification is sent as a push notification to the care recipient;
providing the care recipient access to view the post procedure content through the internal communication channel.

2. The computer-implemented method of claim 1, further comprising:
generating a customizable care plan template for the procedure;
sending the customizable care plan to a user within the care network for the care recipient;
receiving customized care plan data from the user in response to the customizable care plan template;
generating the user specific care plan based on the customizable care plan template.

3. The computer-implemented method of claim 1, further comprising:
receiving care data from the care recipient through the internal communication channel in response to the post procedure content;
determining a user in the care network of the care recipient to send the care data to; determining if the care recipient approves sending of the care data to the user;
if it is determined that the care recipient approves sending of the care data to the user:
sending the care data to the user through the internal communication channel;
sending a second care data received notification to the user through the external communication channel, the second care data received notification being a generic notification lacking any personal health information of the care recipient;
logging in the user to view the care data through the internal communication channel.

4. The computer-implemented method of claim 3, wherein the care data includes health measurements of the care recipient, the health measurement of the care recipient taken by a wearable device of the care recipient.

5. The computer-implemented method of claim 1, further comprising:
determining if the care recipient has been logged in to view the post procedure content with inactivity for a specific amount of time;
if it is determined that the care recipient has been logged in to view the post procedure content with inactivity for a specific amount of time, logging out the care recipient from viewing the post procedure content.

6. The computer-implemented method of claim 1, wherein the post procedure content is sent through the internal communication channel directly to an account associated with a care recipient.

7. The computer-implemented method of claim 1, wherein the post procedure content is posted on a feed that the care recipient can view through the internal communication channel.

8. The computer-implemented method of claim 3, further comprising:
determining the user from care network data and the user specific care plan;
determining second post procedure care conditions for the care data;
sending the care data to the user through the internal communication channel if the second post procedure care conditions are met.

9. The computer-implemented method of claim 3, wherein the user is a doctor who performed the procedure on the care recipient.

10. A system comprising:
a post procedure care network management engine configured to generate a care network for a care recipient in providing post procedure care to the care recipient for a procedure performed on the care recipient;
a user specific care plan management engine configured to generate a user specific care plan for the care recipient, the user specific care plan including post procedure content and first post procedure care conditions associated with the post procedure content;
a care condition determination engine configured to determine if the first post procedure care conditions are satisfied;
an internal messaging engine configured to send the post procedure content to the care recipient through an internal communication channel, if it is determined that the first post procedure care conditions are satisfied;
an external messaging engine configured to send a first care data received notification to the care recipient through an external communication channel that is separate from the internal communication channel and includes at least one of a short message service communication channel, an email communication channel, and a push notification communication channel, the first care data received notification being a generic notification lacking any personal health information of the care recipient and indicating that the care recipient has received the post procedure content through the internal communication channel, wherein the first care data received notification is sent as a push notification to the care recipient, if it is determined that the first post procedure care conditions are satisfied;
a user login engine configured to provide the care recipient access to view the post procedure content through the internal communication channel.

11. The system of claim 10, further comprising:
a customizable care plan template management engine configured to:
generate a customizable care plan template for the procedure;
send the customizable care plan to a user within the care network for the care recipient;
a user specific care plan management engine configured to:
receive customized care plan data from the user in response to the customizable care plan template;
generate the user specific care plan based on the customizable care plan template.

12. The system of claim 10, further comprising:
a care data receipt engine configured to receive care data from the care recipient through the internal communication channel in response to the post procedure content;
a care network recipients determination engine configured to determine a user in the care network of the care recipient to send the care data to;
the internal messaging engine further configured to:
determine if the care recipient approves sending of the care data to the user;
send the care data to the user through the internal communication channel, if it is determined that the care recipient approves sending of the care data to the user;

the external messaging engine further configured to send a second care data received notification to the user through the external communication channel if it is determined that the care recipient approves sending of the care data to the user, the second care data received notification being a generic notification lacking any personal health information of the care recipient;

the user login engine further configured to log in the user to view the care data through the internal communication channel.

13. The system of claim 12, wherein the care data includes health measurements of the care recipient, the health measurement of the care recipient taken by a wearable device of the care recipient.

14. The system of claim 10, wherein the user login engine is further configured to:
determine if the care recipient has been logged in to view the post procedure content with inactivity for a specific amount of time;
if it is determined that the care recipient has been logged in to view the post procedure content with inactivity for a specific amount of time, the user login engine logging out the care recipient from viewing the post procedure content.

15. The system of claim 10, wherein the internal messaging engine is configured to send the post procedure content through the internal communication channel directly to an account associated with a care recipient.

16. The system of claim 10, wherein the internal messaging engine is configured to post the post procedure content on a feed that the care recipient can view through the internal communication channel.

17. The system of claim 12, further comprising:
a care network recipients determination engine configured to determine the user from care network data and the user specific care plan;
a care conditions determination engine configured to determine second post procedure care conditions for the care data;
the internal messaging engine further configured to send the care data to the user through the internal communication channel if the second post procedure care conditions are met.

18. A non-transitory computer-readable storage medium having stored therein instructions which, when executed by a processor, cause the processor to perform operations comprising:
generating a care network for a care recipient in providing post procedure care to the care recipient for a procedure performed on the care recipient;
generating a user specific care plan for the care recipient, the user specific care plan including post procedure content and first post procedure care conditions associated with the post procedure content;
determining if the first post procedure care conditions are satisfied;
if it is determined that the first post procedure care conditions are satisfied:
sending the post procedure content to the care recipient through an internal communication channel;
sending a first care data received notification to the care recipient through an external communication channel that is separate from the internal communication channel and includes at least one of a short message service communication channel, an email communication channel, and a push notification communication channel, the first care data received notification being a generic notification lacking any personal health information of the care recipient and indicating that the care recipient has received the post procedure content through the internal communication channel, wherein the first care data received notification is sent as a push notification to the care recipient;
providing the care recipient access to view the post procedure content through the internal communication channel.

19. The non-transitory computer-readable storage medium of claim 18, wherein the instructions, when executed by a process, further cause the processor to perform operations comprising:
generating a customizable care plan template for the procedure;
sending the customizable care plan to a user within the care network for the care recipient;
receiving customized care plan data from the user in response to the customizable care plan template;
generating the user specific care plan based on the customizable care plan template.

20. The non-transitory computer-readable storage medium of claim 18, wherein the instructions, when executed by a process, further cause the processor to perform operations comprising:
receiving care data from the care recipient through the internal communication channel in response to the post procedure content;
determining a user in the care network of the care recipient to send the care data to;
determining if the care recipient approves sending of the care data to the user; if it is determined that the care recipient approves sending of the care data to the user:
sending the care data to the user through the internal communication channel;
sending a second care data received notification to the user through the external communication channel, the second care data received notification being a generic notification lacking any personal health information of the care recipient;
logging in the user to view the care data through the internal communication channel.

* * * * *